United States Patent
Silver

(10) Patent No.: US 8,249,297 B2
(45) Date of Patent: Aug. 21, 2012

(54) METHOD AND APPARATUS FOR AUTOMATIC VISUAL EVENT DETECTION

(75) Inventor: William M. Silver, Natick, MA (US)

(73) Assignee: Cognex Technology and Investment Corporation, Mt. View, CA (US)

( * ) Notice: Subject to any disclaimer, the term of this patent is extended or adjusted under 35 U.S.C. 154(b) by 898 days.

(21) Appl. No.: 11/138,033

(22) Filed: May 26, 2005

(65) Prior Publication Data

US 2005/0276462 A1    Dec. 15, 2005

Related U.S. Application Data

(63) Continuation of application No. 11/059,512, filed on Feb. 16, 2005, which is a continuation-in-part of application No. 10/865,155, filed on Jun. 9, 2004.

(51) Int. Cl.
*G06K 9/00* (2006.01)
*G06K 9/34* (2006.01)

(52) U.S. Cl. .......................................... 382/103
(58) Field of Classification Search .................. 382/103, 382/107, 141, 154, 173; 348/88, 92, 125, 348/135, 143, 155, 157, 222.1; 707/1–3; 715/804, 810; 717/109, 112, 113
See application file for complete search history.

(56) References Cited

U.S. PATENT DOCUMENTS

| | | |
|---|---|---|
| 4,214,265 A | 7/1980 | Olesen |
| 4,292,666 A | 9/1981 | Hill et al. |
| 4,647,979 A | 3/1987 | Urata |
| 4,847,772 A | 7/1989 | Michalopoulos et al. |
| 4,916,640 A | 4/1990 | Gasperi |
| 4,962,538 A | 10/1990 | Eppler et al. |
| 5,018,213 A | 5/1991 | Sikes |
| 5,040,056 A | 8/1991 | Sager et al. |
| 5,121,201 A * | 6/1992 | Seki ............................. 348/143 |
| 5,146,510 A | 9/1992 | Cox et al. |
| 5,164,998 A | 11/1992 | Reinsch et al. |
| 5,177,420 A | 1/1993 | Wada |
| 5,184,217 A | 2/1993 | Doering |
| 5,198,650 A | 3/1993 | Wike, et al. |

(Continued)

FOREIGN PATENT DOCUMENTS

DE    10012715    9/2000

(Continued)

OTHER PUBLICATIONS

"Cognex VisionPro", *Getting Started—QuickStart Tutorial*, Cognex Corporation, 590-6560, Revision 3.5,(May, 2004),69-94.

(Continued)

*Primary Examiner* — Amir Alavi

(57) ABSTRACT

Disclosed are methods and apparatus for automatic visual detection of events, for recording images of those events and retrieving them for display and human or automated analysis, and for sending synchronized signals to external equipment when events are detected. An event corresponds to a specific condition, among some time-varying conditions within the field of view of an imaging device, that can be detected by visual means based on capturing and analyzing digital images of a two-dimensional field of view in which the event may occur. Events may correspond to rare, short duration mechanical failures for which obtaining images for analysis is desirable. Events are detected by considering evidence obtained from an analysis of multiple images of the field of view, during which time moving mechanical components can be seen from multiple viewing perspectives.

17 Claims, 12 Drawing Sheets

U.S. PATENT DOCUMENTS

| | | | |
|---|---|---|---|
| 5,210,798 A * | 5/1993 | Ekchian et al. | 382/103 |
| 5,233,541 A * | 8/1993 | Corwin et al. | 348/81 |
| 5,262,626 A | 11/1993 | Goren et al. | |
| 5,286,960 A | 2/1994 | Longacre et al. | |
| 5,298,697 A | 3/1994 | Suzuki et al. | |
| 5,317,645 A | 5/1994 | Perozek et al. | |
| 5,345,515 A | 9/1994 | Nishi et al. | |
| 5,365,596 A | 11/1994 | Dante et al. | |
| 5,420,409 A | 5/1995 | Longacre et al. | |
| 5,476,010 A | 12/1995 | Fleming et al. | |
| 5,481,712 A | 1/1996 | Silver | |
| 5,581,625 A | 12/1996 | Connell | |
| 5,687,249 A | 11/1997 | Kato | |
| 5,717,834 A | 2/1998 | Werblin et al. | |
| 5,734,742 A | 3/1998 | Asaeda et al. | |
| 5,742,037 A | 4/1998 | Scola et al. | |
| 5,751,831 A * | 5/1998 | Ono | 382/103 |
| 5,802,220 A | 9/1998 | Black et al. | |
| 5,809,161 A | 9/1998 | Auty et al. | |
| 5,825,483 A | 10/1998 | Michael et al. | |
| 5,852,669 A * | 12/1998 | Eleftheriadis et al. | 382/118 |
| 5,872,354 A | 2/1999 | Hanson | |
| 5,929,418 A | 7/1999 | Ehrhart et al. | |
| 5,932,862 A | 8/1999 | Hussey et al. | |
| 5,937,096 A | 8/1999 | Kawai | |
| 5,942,741 A | 8/1999 | Longacre et al. | |
| 5,943,432 A | 8/1999 | Gilmore et al. | |
| 5,960,097 A | 9/1999 | Pfeiffer et al. | |
| 5,960,125 A | 9/1999 | Michael et al. | |
| 6,046,764 A | 4/2000 | Kirby et al. | |
| 6,049,619 A | 4/2000 | Anandan et al. | |
| 6,061,471 A * | 5/2000 | Coleman, Jr. | 382/173 |
| 6,072,494 A | 6/2000 | Nguyen | |
| 6,072,882 A | 6/2000 | White et al. | |
| 6,078,251 A | 6/2000 | Landt et al. | |
| 6,088,467 A | 7/2000 | Sarpeshkar et al. | |
| 6,115,480 A * | 9/2000 | Washizawa | 382/103 |
| 6,158,661 A | 12/2000 | Chadima, Jr. et al. | |
| 6,160,494 A | 12/2000 | Sodi et al. | |
| 6,161,760 A | 12/2000 | Marrs | |
| 6,169,535 B1 | 1/2001 | Lee | |
| 6,173,070 B1 | 1/2001 | Michael et al. | |
| 6,175,644 B1 | 1/2001 | Scola et al. | |
| 6,184,924 B1 | 2/2001 | Schneider et al. | |
| 6,215,892 B1 | 4/2001 | Douglass et al. | |
| 6,282,462 B1 | 8/2001 | Hopkins | |
| 6,285,787 B1 | 9/2001 | Kawachi et al. | |
| 6,298,176 B2 | 10/2001 | Longacre, Jr. et al. | |
| 6,301,610 B1 | 10/2001 | Ramser et al. | |
| 6,333,993 B1 * | 12/2001 | Sakamoto | 382/173 |
| 6,346,966 B1 | 2/2002 | Toh | |
| 6,347,762 B1 | 2/2002 | Sims et al. | |
| 6,360,003 B1 | 3/2002 | Doi et al. | |
| 6,396,517 B1 | 5/2002 | Beck et al. | |
| 6,396,949 B1 | 5/2002 | Nichani | |
| 6,408,429 B1 | 6/2002 | Marrion, Jr. et al. | |
| 6,446,868 B1 | 9/2002 | Robertson et al. | |
| 6,483,935 B1 | 11/2002 | Rostami et al. | |
| 6,487,304 B1 | 11/2002 | Szeliski | |
| 6,525,810 B1 | 2/2003 | Kipman | |
| 6,526,156 B1 | 2/2003 | Black et al. | |
| 6,539,107 B1 | 3/2003 | Michael et al. | |
| 6,545,705 B1 | 4/2003 | Sigel et al. | |
| 6,549,647 B1 | 4/2003 | Skunes et al. | |
| 6,573,929 B1 | 6/2003 | Glier et al. | |
| 6,580,810 B1 | 6/2003 | Yang et al. | |
| 6,587,122 B1 | 7/2003 | King et al. | |
| 6,597,381 B1 | 7/2003 | Eskridge et al. | |
| 6,608,930 B1 * | 8/2003 | Agnihotri et al. | 382/176 |
| 6,618,074 B1 | 9/2003 | Seeley et al. | |
| 6,621,571 B1 | 9/2003 | Maeda et al. | |
| 6,628,805 B1 | 9/2003 | Hansen et al. | |
| 6,629,642 B1 | 10/2003 | Swartz et al. | |
| 6,646,244 B2 | 11/2003 | Aas et al. | |
| 6,668,075 B1 | 12/2003 | Nakamura | |
| 6,677,852 B1 | 1/2004 | Landt | |
| 6,741,977 B1 * | 5/2004 | Nagaya et al. | 707/1 |
| 6,753,876 B2 | 6/2004 | Brooksby et al. | |
| 6,761,316 B2 | 7/2004 | Bridgelall | |
| 6,774,917 B1 | 8/2004 | Foote et al. | |
| 6,816,063 B2 | 11/2004 | Kubler | |
| 6,919,793 B2 | 7/2005 | Heinrich | |
| 6,944,584 B1 | 9/2005 | Tenney et al. | |
| 6,973,209 B2 | 12/2005 | Tanaka | |
| 6,985,827 B2 | 1/2006 | Williams et al. | |
| 6,987,528 B1 | 1/2006 | Nagahisa et al. | |
| 6,997,556 B2 * | 2/2006 | Pfleger | 351/246 |
| 6,999,625 B1 * | 2/2006 | Nelson | 382/224 |
| 7,062,071 B2 * | 6/2006 | Tsujino et al. | 382/103 |
| 7,066,388 B2 | 6/2006 | He | |
| 7,070,099 B2 | 7/2006 | Patel | |
| 7,085,401 B2 * | 8/2006 | Averbuch et al. | 382/103 |
| 7,088,387 B1 | 8/2006 | Freeman et al. | |
| 7,088,846 B2 * | 8/2006 | Han et al. | 382/103 |
| 7,181,066 B1 | 2/2007 | Wagman | |
| 7,227,978 B2 | 6/2007 | Komatsuzaki et al. | |
| 7,266,768 B2 | 9/2007 | Ferlitsch et al. | |
| 7,274,808 B2 | 9/2007 | Baharav et al. | |
| 7,280,685 B2 | 10/2007 | Beardsley et al. | |
| 7,604,174 B2 | 10/2009 | Gerst et al. | |
| 7,657,081 B2 | 2/2010 | Blais et al. | |
| 2001/0042789 A1 | 11/2001 | Krichever et al. | |
| 2002/0005895 A1 | 1/2002 | Freeman et al. | |
| 2002/0099455 A1 | 7/2002 | Ward | |
| 2002/0122582 A1 | 9/2002 | Masuda et al. | |
| 2002/0177918 A1 | 11/2002 | Pierel et al. | |
| 2002/0181405 A1 | 12/2002 | Ying | |
| 2002/0196336 A1 | 12/2002 | Batson et al. | |
| 2002/0196342 A1 | 12/2002 | Walker et al. | |
| 2003/0062418 A1 | 4/2003 | Barber et al. | |
| 2003/0113018 A1 | 6/2003 | Nefian et al. | |
| 2003/0120714 A1 | 6/2003 | Wolff et al. | |
| 2003/0137590 A1 | 7/2003 | Barnes et al. | |
| 2003/0219146 A1 | 11/2003 | Jepson et al. | |
| 2003/0227483 A1 | 12/2003 | Schultz et al. | |
| 2004/0148057 A1 | 7/2004 | Breed et al. | |
| 2004/0218806 A1 | 11/2004 | Miyamoto et al. | |
| 2005/0226490 A1 | 10/2005 | Phillips et al. | |
| 2005/0275728 A1 | 12/2005 | Mirtich et al. | |
| 2005/0275831 A1 | 12/2005 | Silver | |
| 2005/0275833 A1 | 12/2005 | Silver | |
| 2005/0275834 A1 | 12/2005 | Silver | |
| 2005/0276445 A1 * | 12/2005 | Silver et al. | 382/103 |
| 2005/0276459 A1 | 12/2005 | Eames et al. | |
| 2005/0276461 A1 * | 12/2005 | Silver et al. | 382/141 |
| 2005/0276462 A1 * | 12/2005 | Silver et al. | 382/141 |
| 2006/0022052 A1 | 2/2006 | Patel et al. | |
| 2006/0107211 A1 | 5/2006 | Mirtich et al. | |
| 2006/0107223 A1 | 5/2006 | Mirtich et al. | |
| 2006/0131419 A1 | 6/2006 | Nunnink | |
| 2006/0133757 A1 | 6/2006 | Nunnink | |
| 2006/0146337 A1 | 7/2006 | Marshall et al. | |
| 2006/0223628 A1 | 10/2006 | Walker et al. | |
| 2006/0249581 A1 | 11/2006 | Smith et al. | |
| 2006/0249587 A1 | 11/2006 | Choi et al. | |
| 2006/0283952 A1 | 12/2006 | Wang | |
| 2007/0009152 A1 | 1/2007 | Kanda | |
| 2007/0146491 A1 | 6/2007 | Tremblay et al. | |
| 2007/0181692 A1 | 8/2007 | Barkan et al. | |
| 2008/0004822 A1 | 1/2008 | Nadabar et al. | |
| 2008/0011855 A1 | 1/2008 | Nadabar | |
| 2008/0036873 A1 | 2/2008 | Silver | |
| 2008/0063245 A1 | 3/2008 | Benkley et al. | |
| 2008/0166015 A1 | 7/2008 | Haering et al. | |
| 2008/0167890 A1 | 7/2008 | Pannese et al. | |
| 2008/0205714 A1 | 8/2008 | Benkley | |
| 2008/0219521 A1 | 9/2008 | Benkley | |
| 2008/0226132 A1 | 9/2008 | Gardner | |
| 2008/0285802 A1 | 11/2008 | Bramblet et al. | |
| 2009/0121027 A1 | 5/2009 | Nadabar | |
| 2009/0154779 A1 | 6/2009 | Satyan et al. | |
| 2010/0241981 A1 | 9/2010 | Mirtich et al. | |
| 2010/0318936 A1 | 12/2010 | Tremblay et al. | |

FOREIGN PATENT DOCUMENTS

| | | |
|---|---|---|
| EP | 0939382 | 9/1999 |
| EP | 0815688 B1 | 5/2000 |

| | | |
|---|---|---|
| EP | 0896290 | 10/2004 |
| EP | 1469420 | 10/2004 |
| EP | 1975849 | 10/2008 |
| GB | 2226130 | 6/1990 |
| GB | 2309078 | 7/1997 |
| JP | 60147602 | 8/1985 |
| JP | 09185710 | 7/1997 |
| JP | 2000-84495 | 3/2000 |
| JP | 2000298103 | 10/2000 |
| JP | 2002214153 | 7/2002 |
| JP | 2002318202 | 10/2002 |
| JP | 2003270166 | 9/2003 |
| JP | 2004145504 | 5/2004 |
| WO | WO 96/09597 | 3/1996 |
| WO | WO-0141068 | 6/2001 |
| WO | WO-0215120 | 2/2002 |
| WO | WO-02075637 | 9/2002 |
| WO | WO-03102859 | 12/2003 |
| WO | WO-2008118419 | 10/2008 |
| WO | WO-2008118425 | 10/2008 |

OTHER PUBLICATIONS

Haering, N., et al., "Visual Event Detection", *Kluwer Academic Publishers*, Chapter 2, Section 8,(2001).

IBM, "Software Controls for Automated Inspection Device Used to Check Interposer Buttons for Defects", *IP.com Journal, IP.com Inc.*, West Henrietts, NY, US, (Mar. 27, 2003).

Uno, T., et al., "A Method of Real-Time Recognition of Moving Objects and its Application", *Pattern Recognition; Pergamon Press*, vol. 8, pp. 201-208, (1976),pp. 201-208.

"Bi-i", *AnaLogic Computers Ltd.*

"Bi-i: Bio-inspired Real-Time Very High Speed Image Processing Systems", *AnaLogic Computers Ltd.*, http://www.analogic-computers.com/cgi-bin/phprint21.php.

"Cellular device processes at ultrafast speeds", *VisionSystems Design*, (Feb. 2003).

West, Perry C., "High Speed, Real-Time Machine Vision", *Imagenation and Automated Vision Systems, Inc.*, (2001).

Wilson, Andrew, "CMOS/CCD sensors spot niche applications", *Vision Systems Design*, (Jun. 2003).

Zarandy, Akos, et al., "Ultra-High Frame Rate Focal Plane Image Sensor and Processor", *IEEE Sensors Journal*, vol. 2, No. 6,(2002).

Zarandy, A., et al., "Vision Systems Based on the 128X128 Focal Plane Cellular Visual Microprocessor Chips", *IEEE*, (Mar. 2003),III-518-III-521.

Shane C. Hunt, Mastering Microsoft PhotoDraw 2000, SYBEX, Inc., May 21, 1999.

Integrated Design Tools, High-Speed CMOS Digital Camera, X-Stream Vision User's Manual, 2000.

IO Industries, High Speed Digital Video Recording Software 4.0, IO industries, Inc.-Ontario, CA, 2002.

Phillip Kahn, Building Blocks for Computer Vision Systems, IEEE Expert, vol. 8, No. 6, XP002480004, pp. 40-50, Dec. 6, 1993.

Matrox, Interactive Windows Imaging Software for Industrial and Scientific Applications, Inspector 4.0—Matrox Imaging, pp. 8, Apr. 15, 2002.

Olympus Industrial, Design Philosophy, i-speed.

Olympus Industrial, High Speed, High Quality Imaging Systems, i-speed Product Brochure—Publisher Olympus Industrial.

RVSI, Smart Camera Reader for Directly Marked Data Matrix Codes, HawkEye 1515 with GUI.

Whelan, P. et al., Machine Vision Algorithms in Java, Chapter 1—An Introduction to Machine Vision, Springer-Verlag, XP002480005, 2001.

Photron, USA, Product information for FASTCAM-X 1280 PCI, Copyright 2004, www.photron.com.

Photron, USA, Product information for FASTCAM PCI, Copyright 2004, www.photron.com.

Photron, USA, Product information for Ultima 1024, Copyright 2004, www.photron.com.

Photron, USA, Product information for Ultima 512, Copyright 2004, www.photron.com.

Photron, USA, Product information for Ultima APX, Copyright 2004, www.photron.com.

KSV Instruments Ltd., HiSIS 2002—High Speed Imaging System, www.ksvltd.fi, 2004.

Cognex Corporation 3000/4000/5000 Image Processing, Revision 7.4 590-0135 Edge Detection Tool, 1996.

Cognex Corporation 4000/5000 SMD Placement Guidance Package, User's Manual, Release 3.8.00, Chapter 15, 1998.

Cognex Corporation, CVL Vision Tools Guide, Cognex MVS-8000 Series, Chapter 5, Symbol Tool, CVL 5.4, Dec. 1999.

Adaptive Optics Associates, Laser Scanning Product Guide, Industrial Products and Systems, Mar. 2003.

Wright, Anne, et al, Cognachrome Vision System User's Guide, Newton Research Labs, Manual Edition 2.0, Documents Software Version 26.0, Jun. 3, 1996.

Stemmer Imaging Gmb-H, Going Multimedia with Common Vision Blox, Product News, www.stemmer-imaging.de, http://www.imasys.fr/pages/news/item.php?view=319&item=313, Feb. 20, 2003.

Cordin Company, Electronic Imaging Systems, High Speed Imaging Solutions: 200-500 Series Cameras, www.cordin.com, 2004.

"ADSP-BF533 Blackfin Processor Hardware Reference", *Analog Devices Inc.—Media Platforms and Services Group*, Preliminary Revision—Part No. 82-002005-01,(Mar. 2003).

"Blackfin Processor Instruction Set Reference", *Analog Devices, Inc.*, Revision 2.0, Part No. 82-000410-14,(May, 2003).

"LM9630 100 x 128, 580 fps UltraSensitive Monochrome CMOS Image Sensor", *National Semiconductor Corp.*, www.national.com Rev. 1.0,(Jan. 2004).

The International Search Report and Written Opinion of the International Searching Authority, International Application No. PCT/US2005/019923 dated Jan. 19, 2006.

Singapore Patent Application No. 200608485-9, 1st Written Opinion, Australian Patent Office, dated Feb. 15, 2008.

European Patent Application No., 05 758 780.0, Communication pursuant to 94(3) EPC, dated Mar. 25, 20009.

Singapore Patent Application No. 200608485-9, 2nd Written Opinion, Australian Patent Office, dated Sep. 24, 2008.

European Patent Application No., 05 758 780.0, Communication pursuant to 94(3) EPC, Mar. 25, 2009.

The International Search Report and Written Opinion of the International Searching Authority, International Application No. PCT/US2005/019923, Jan. 9, 2006.

Australian Patent Office, Singapore Patent Application No. 200608485-9, 1st Written Opinion, Feb. 15, 2008.

Australian Patent Office, Singapore Patent Application No. 200608485-9, 2nd Written Opinion, Sep. 24, 2008.

"CCD/CMOS Sensors Spot Niche Application", *PennWell Corporation*, Vision System Design—Imaging and Machine Vision Technology, (2004).

"CV-2100 Series", *Keyence America*http://www.keyence.com/products/vision/cv_2100_spec.html, High-Speed Digital Machine Vision System, 2004.

"HawkEye 1515—Smart Camera Reader for Directly Marked Data Matrix Codes", *RVSI 486 Amherst Street Nashua, NH03063*. 2003.

"ICS 100—Intelligent Camera Sensor", *SICK Product Information*, SICK Industrial Sensors 6900 West 110th Street Minneapolis, MN 55438 www.sickusa.com, 2004.

"iQ 180", *Adaptive Optics Associates 900 Coles Road Blackwood, NJ08012-4683*, (Dec. 2003).

"Laser Scanning Product Guide", *Adaptive Optics Associates—Industrial Products and Systems 90 Coles Road Blackwood, NJ08012*, Industrial Holographic and Conventional Laser 1D, Omnidirectional Bar Codes Scanners,(Mar. 2003).

"Matsushita Imagecheckers", *NAiS Machine Vision—Matsushita Machine Vision Systems*(2003).

"Matsushita LightPix AE10", NAiS Machine Vision—Matsushita Machine Vision Systems (2003).

"Simatic Machine Vision", *Simatic VS 100 Series Siemens AG*, www.siemens.com/machine-vision,(Apr. 1, 2003).

"SmartCapture Tool", *Feature Fact Sheet, Visionx Inc.*, www.visionxinc.com, (2003).

Asundi, A., et al., "High-Speed TDI Imaging for Peripheral Inspection", *Proc. SPIE* vol. 2423, Machine Vision Applications in Idustrial Inspection III, Frederick Y. Wu; Stephen S. Wilson; Eds., (Mar. 1995), 189-194.

Baillard, C., et al., "Automatic Reconstruction of Piecewise Planar Models from Multiple Views", *CVPR*, vol. 02, No. 2,(1999), 2559.

Baumberg, A. M., et al., "Learning Flexible Models from Image Sequences", *University of Leeds, School of Computer Studies, Research Report Series, Report 93,36,* (Oct. 1993), pp. 1-13.

Chang, Dingding et al., "Feature Detection of Moving Images using a Hierarchical Relaxation Method", *IEICE TRANS. INF, & SYST.,* vol. E79-D, (Jul. 7, 1996).

Corke, Peter I., et al., "Real Time Industrial Machine Vision", *Electrical Engineering Congress Sydney, Australia,* CSIRO Division on Manufacturing Technology,(1994).

Demotte, Donald, "Visual Line Tracking", *Application Overview & Issues Machine Vision for Robot Guidance Workshop*, (May 5, 2004).

Kim, Zuwhan, et al., "Automatic Description of Complex Buildings with Multiple Images", IEEE 0-7695-0813-8/00. (2000), 155-162.

Marsh, R, et al., "The application of knowledge based vision to closed-loop control of the injection molding process", *SPIE* vol. 3164, Faculty of Engineering University of the West of England United Kingdon, (1997), 605-16.

Rohr, K., "Incremental Recognition of Pedestrians from Image Sequences", *CVPR93*(1993).

Stauffer, Chris, et al., "Tracking-Based Automatic Object Recognition", *Artificial Intelligence Laboratory, Massachusetts Institute of Technology, Cambridge, MA* http://www.ai.mit.edu, pp. 133-134 2003.

Di Mauro, E. C., et al., "Check—a generic and specific industrial inspection tool", *IEE Proc.-Vis. Image Signal Process.*, vol. 143, No. 4,(Aug. 27, 1996),pp. 241-249.

Apple Computer Inc., Studio Display User's Manual online, retrieved on Nov. 24, 2010, retrieved from the Internet http://manuals.info.apple.com/en/studioDisplay_15inLCDUserManual.pdf, (1998).

Cognex Corporation, VisionPro Getting Started, Revision 3.2, Chapter 5, 590-6508, copyright 2003.

Cognex Corporation, 3000/4000/5000 Vision Tools, revision 7.6, 590-0136, Chapter 13, 1996.

Cognex Corporation, Cognex 3000/4000/5000, Vision Tools, Revision 7.6, 590-0136, Chapter 10 Auto-Focus, (1996).

Cognex Corporation, VisionPro Getting Started, Revision 3.2, 590-6508, copyright 2003.

Prosecution file history for U.S. Appl. No. 10/865,155, dated May 11, 2005 through Jan. 9, 2012.

Prosecution file history for U.S. Appl. No. 11/136,019, dated May 24, 2005 through Oct. 29, 2010.

Prosecution file history for U.S. Appl. No. 11/136,103, dated May 24, 2005 through Nov. 2, 2011.

Prosecution file history for U.S. Appl. No. 11/769,494, dated Jun. 27, 2007 through Jan. 11, 2012.

Prosecution file history for U.S. Appl. No. 11/059,512 through Dec. 18, 2008.

Prosecution file history for U.S. Appl. No. 11/138,023 dated May 26, 2005 through Nov. 20, 2009.

Prosecution file history for U.S. Appl. No. 11/138,025 dated May 26, 2005 through Dec. 28, 2011.

U.S. Appl. No. 12/758,455, filed Apr. 12, 2010.

U.S. Appl. No. 12/931,504, filed Dec. 22, 2010, Mirtich, Eames.

Chen, Y. H., "Computer Vision for General Purpose Visual Inspection: a Fuzzy Logic Approach", *Optics and Lasers in Engineering 22*, Elsevier Science Limited, vol. 22, No. 3,(1995), pp. 182-192.

Denis, Jolivet, "LabVIEW and IMAQ Vision Builder Provide Automated Visual Test System", *Semiconductor: IMAQ Advanced Analysis Toolkit*, IMAQ Vision Builder—LabVIEW—National Instruments—XP002356529—URL http://www.ni.com/pdf/csma/us/Jndeswg.pdf, 1996.

Di Mauro, E. C., et al., "Check—a generic and specific industrial inspection tool", *IEE Proc.-Vis. Image Signal Process.*, vol. 143, No. 4,(Aug. 27, 1996), pp. 241-249.

National Instruments, "IMAQVision Builder Tutorial", IMAQ XP-002356530, http://www.ni.com/pdf/manuals/322228c.pdf,(Dec. 2000).

Office Action, Japanese patent application No. 2007-527620, dated Mar. 28, 2012.

\* cited by examiner

| symbol | description | example |
|---|---|---|
| n | total number of candidate frames | 12 |
| d | number of active frames | 11 |
| p | percent of candidate frames that are active | 91.7 |
| w | total event detection weight | 9.7 |
| a | mean event detection weight | 0.81 |
| m | median event detection weight | 0.92 |

METHOD AND APPARATUS FOR AUTOMATIC VISUAL EVENT DETECTION

CROSS REFERENCE TO RELATED APPLICATIONS

This application is a continuation of application Ser. No. 11/059,512 filed on Feb. 16, 2005, now abandoned, which is a continuation-in-part to U.S. patent application Ser. No. 10/865,155, filed Jun. 9, 2004.

RELATED APPLICATION

This application is a continuation-in-part of co-pending U.S. patent application Ser. No. 10/865,155, entitled METHOD AND APPARATUS FOR VISUAL DETECTION AND INSPECTION OF OBJECTS, by William M. Silver, filed Jun. 9, 2004, the teachings of which are expressly incorporated herein by reference, and referred to herein as the "Vision Detector Method and Apparatus".

BACKGROUND OF THE INVENTION

1. Field of the Invention

The invention relates to high-speed video event detection, motion analysis, image recording, and automated image analysis.

2. Description of the Related Art

It is well-known in the art to use high-speed image recording devices for motion analysis of mechanical systems that operate too fast for the human eye to see. These devices capture and record hundreds or thousands of images per second of some mechanical process, and then display those images, in slow motion or as still pictures, for human users to see and analyze the high-speed mechanical motions.

Of particular interest is recording rare, short-duration mechanical events that may cause failures in the mechanical process. The fact that these events are both rare and short-duration creates special challenges. Suppose, for example, that the image recording device records 1000 images per second, the event lasts three milliseconds, and occurs on average once an hour. Without some additional mechanism, the human user would need to look at, on average, 3.6 million pictures to find the two or three that contain the event.

It is well-known in the art to address this challenge by providing a trigger signal for the image recording device that indicates when the event has occurred. The image recording device keeps a limited number of the most recent images, say the last one second of recording, and when the trigger signal indicates that the event has occurred, records for a brief additional time and then stops. This gives the user a relatively small number of images to look at both before and after the event. Furthermore, the user knows exactly when each image was captured relative to the time of the event as indicated by the trigger signal.

Clearly, the success of this method depends on being able to generate a suitable trigger signal. It is well-known in the art to use a photodetector for this purpose. A typical photodetector has a light source and a single photoelectric sensor that responds to the intensity of light that is reflected by a point on the surface of an object, or transmitted along a path that an object may cross. A user-adjustable sensitivity threshold establishes a light intensity above which (or below which) an output signal of the photodetector will be energized.

It is often the case that multiple photodetectors are needed to provide the trigger signal. For example, if the mechanical process is a manufacturing line producing discrete objects, and the event corresponds to the production of an object with a missing component, then at least two photodetectors are needed: one to detect that an object is present, and the other to detect the missing component. Sometimes even more than two are needed to detect complex events.

Using photodetectors to provide a trigger signal has some limitations, however, including
- a simple measure of the intensity of light transmitted or reflected by one or more points may be insufficient for detecting the event;
- it can be difficult to adjust the position of each photodetector so that it is looking at the exact right point;
- the points to be measured must not move around during normal operation of the mechanical process; and
- the need for multiple photodetectors can make installation and setup difficult.

It is also known in the art to use a machine vision system to provide a trigger signal. A machine vision system is a device that can capture a digital image of a two-dimensional field of view, and then analyze the image and make decisions. The image is captured by exposing a two-dimensional array of photosensitive elements for a brief period, called the integration or shutter time, to light that has been focused on the array by a lens. The array is called an imager and the individual elements are called pixels. Each pixel measures the intensity of light falling on it during the shutter time. The measured intensity values are then converted to digital numbers and stored in the memory of the vision system to form the image, which is analyzed by a digital processing element such as a computer, using methods well-known in the art to make decisions.

A machine vision system can avoid the limitations of photodetectors. One machine vision system can replace many photodetectors and make sophisticated measurements of extended brightness patterns, instead of just single-point intensity measurements. Adjusting the positions looked at can be done using a graphical user interface instead of a screwdriver and wrench, and those positions can be relocated for each image based on the content of the image itself.

A machine vision system has its own limitations, however, including:
- machine vision systems are generally only suitable when the event relates to the inspection of discrete objects; and
- machine vision systems are generally too slow to detect short-duration events, and must instead look for some long-duration condition caused by that event, such as a defective product.

Note that when used to provide a trigger signal, a machine vision system is separate from the high-speed image recording device. It does not see and cannot analyze the images captured by that device, the very images that contain the event that is to be detected. Even if those images could be made available to a machine vision system, they are produced at far too high a rate to be analyzed by machine vision systems of conventional design.

The Vision Detector Method and Apparatus teaches novel methods and systems that can overcome the above-described limitations of prior art photodetectors and machine vision systems for detecting that a triggering event has occurred. These teachings also provide fertile ground for innovation leading to improvements beyond the scope of the original teachings. In the following section the Vision Detector Method and Apparatus is briefly summarized, and a subsequent section lays out the problems to be addressed by the present invention.

Vision Detector Method and Apparatus

The Vision Detector Method and Apparatus provides systems and methods for automatic optoelectronic detection and inspection of objects, based on capturing digital images of a two-dimensional field of view in which an object to be detected or inspected may be located, and then analyzing the images and making decisions. These systems and methods analyze patterns of brightness reflected from extended areas, handle many distinct features on the object, accommodate line changeovers through software means, and handle uncertain and variable object locations. They are less expensive and easier to set up than prior art machine vision systems, and operate at much higher speeds. These systems and methods furthermore make use of multiple perspectives of moving objects, operate without triggers, provide appropriately synchronized output signals, and provide other significant and useful capabilities that will be apparent to those skilled in the art.

One aspect of the Vision Detector Method and Apparatus is an apparatus, called a vision detector, that can capture and analyze a sequence of images at higher speeds than prior art vision systems. An image in such a sequence that is captured and analyzed is called a frame. The rate at which frames are captured and analyzed, called the frame rate, is sufficiently high that a moving object is seen in multiple consecutive frames as it passes through the field of view (FOV). Since the objects moves somewhat between successive frames, it is located in multiple positions in the FOV, and therefore it is seen from multiple viewing perspectives and positions relative to the illumination.

Another aspect of the Vision Detector Method and Apparatus is a method, called dynamic image analysis, for inspecting objects by capturing and analyzing multiple frames for which the object is located in the field of view, and basing a result on a combination of evidence obtained from each of those frames. The method provides significant advantages over prior art machine vision systems that make decisions based on a single frame.

Yet another aspect of the Vision Detector Method and Apparatus is a method, called visual event detection, for detecting events that may occur in the field of view. An event can be an object passing through the field of view, and by using visual event detection the object can be detected without the need for a trigger signal.

Additional aspects of the Vision Detector Method and Apparatus will be apparent by a study of the figures and detailed descriptions given therein.

In order to obtain images from multiple perspectives, it is desirable that an object to be detected or inspected moves no more than a small fraction of the field of view between successive frames, often no more than a few pixels. According to the Vision Detector Method and Apparatus, it is generally desirable that the object motion be no more than about one-quarter of the FOV per frame, and in typical embodiments no more than 5% or less of the FOV. It is desirable that this be achieved not by slowing down a manufacturing process but by providing a sufficiently high frame rate. In an example system the frame rate is at least 200 frames/second, and in another example the frame rate is at least 40 times the average rate at which objects are presented to the vision detector.

An exemplary system is taught that can capture and analyze up to 500 frames/second. This system makes use of an ultra-sensitive imager that has far fewer pixels than prior art vision systems. The high sensitivity allows very short shutter times using very inexpensive LED illumination, which in combination with the relatively small number of pixels allows very short image capture times. The imager is interfaced to a digital signal processor (DSP) that can receive and store pixel data simultaneously with analysis operations. Using methods taught therein and implemented by means of suitable software for the DSP, the time to analyze each frame generally can be kept to within the time needed to capture the next frame. The capture and analysis methods and apparatus combine to provide the desired high frame rate. By carefully matching the capabilities of the imager, DSP, and illumination with the objectives of the invention, the exemplary system can be significantly less expensive than prior art machine vision systems.

The method of visual event detection involves capturing a sequence of frames and analyzing each frame to determine evidence that an event is occurring or has occurred. When visual event detection is used to detect objects without the need for a trigger signal, the analysis would determine evidence that an object is located in the field of view.

In an exemplary method the evidence is in the form of a value, called an object detection weight, that indicates a level of confidence that an object is located in the field of view. The value may be a simple yes/no choice that indicates high or low confidence, a number that indicates a range of levels of confidence, or any item of information that conveys evidence. One example of such a number is a so-called fuzzy logic value, further described therein. Note that no machine can make a perfect decision from an image, and so will instead make judgments based on imperfect evidence.

When performing object detection, a test is made for each frame to decide whether the evidence is sufficient that an object is located in the field of view. If a simple yes/no value is used, the evidence may be considered sufficient if the value is "yes". If a number is used, sufficiency may be determined by comparing the number to a threshold. Frames where the evidence is sufficient are called active frames. Note that what constitutes sufficient evidence is ultimately defined by a human user who configures the vision detector based on an understanding of the specific application at hand. The vision detector automatically applies that definition in making its decisions.

When performing object detection, each object passing through the field of view will produce multiple active frames due to the high frame rate of the vision detector. These frames may not be strictly consecutive, however, because as the object passes through the field of view there may be some viewing perspectives, or other conditions, for which the evidence that the object is located in the field of view is not sufficient. Therefore it is desirable that detection of an object begins when an active frame is found, but does not end until a number of consecutive inactive frames are found. This number can be chosen as appropriate by a user.

Once a set of active frames has been found that may correspond to an object passing through the field of view, it is desirable to perform a further analysis to determine whether an object has indeed been detected. This further analysis may consider some statistics of the active frames, including the number of active frames, the sum of the object detection weights, the average object detection weight, and the like.

The method of dynamic image analysis involves capturing and analyzing multiple frames to inspect an object, where "inspect" means to determine some information about the status of the object. In one example of this method, the status of an object includes whether or not the object satisfies inspection criteria chosen as appropriate by a user.

In some aspects of the Vision Detector Method and Apparatus dynamic image analysis is combined with visual event detection, so that the active frames chosen by the visual event detection method are the ones used by the dynamic image analysis method to inspect the object. In other aspects of the Vision Detector Method and Apparatus, the frames to be used by dynamic image analysis can be captured in response to a trigger signal.

Each such frame is analyzed to determine evidence that the object satisfies the inspection criteria. In one exemplary method, the evidence is in the form of a value, called an object pass score, that indicates a level of confidence that the object satisfies the inspection criteria. As with object detection weights, the value may be a simple yes/no choice that indicates high or low confidence, a number, such as a fuzzy logic value, that indicates a range of levels of confidence, or any item of information that conveys evidence.

The status of the object may be determined from statistics of the object pass scores, such as an average or percentile of the object pass scores. The status may also be determined by weighted statistics, such as a weighted average or weighted percentile, using the object detection weights. Weighted statistics effectively weight evidence more heavily from frames wherein the confidence is higher that the object is actually located in the field of view for that frame.

Evidence for object detection and inspection is obtained by examining a frame for information about one or more visible features of the object. A visible feature is a portion of the object wherein the amount, pattern, or other characteristic of emitted light conveys information about the presence, identity, or status of the object. Light can be emitted by any process or combination of processes, including but not limited to reflection, transmission, or refraction of a source external or internal to the object, or directly from a source internal to the object.

One aspect of the Vision Detector Method and Apparatus is a method for obtaining evidence, including object detection weights and object pass scores, by image analysis operations on one or more regions of interest in each frame for which the evidence is needed. In an example of this method, the image analysis operation computes a measurement based on the pixel values in the region of interest, where the measurement is responsive to some appropriate characteristic of a visible feature of the object. The measurement is converted to a logic value by a threshold operation, and the logic values obtained from the regions of interest are combined to produce the evidence for the frame. The logic values can be binary or fuzzy logic values, with the thresholds and logical combination being binary or fuzzy as appropriate.

For visual event detection, evidence that an object is located in the field of view is effectively defined by the regions of interest, measurements, thresholds, logical combinations, and other parameters further described herein, which are collectively called the configuration of the vision detector and are chosen by a user as appropriate for a given application of the invention. Similarly, the configuration of the vision detector defines what constitutes sufficient evidence.

For dynamic image analysis, evidence that an object satisfies the inspection criteria is also effectively defined by the configuration of the vision detector.

Discussion of the Problem

Given the limitations of photodetectors and machine vision systems in providing triggers for high-speed event detection, motion analysis, and image recording, there is a need for improved methods and systems that avoid the need for a trigger signal by providing high-speed visual event detection and integrating it with high-speed image recording.

The Vision Detector Method and Apparatus teaches novel image analysis methods and systems that provide, among other benefits, high-speed visual event detection, but without teaching any integration with image recording for use in motion analysis. Thus there is a need for improved methods and systems that combine suitable elements and configurations of the Vision Detector Method and Apparatus with suitable image recording and display capabilities to achieve novel and useful methods and systems for automatic visual detection, recording, and retrieval of events.

Furthermore, the Vision Detector Method and Apparatus provides illustrative embodiments of visual event detection that are primarily intended to detect events corresponding to discrete objects passing through the field of view. While it will be clear to one of ordinary skill that these teachings may be used to detect other types of events, improvements not taught therein may also be useful in detecting such events. Thus there is a need to expand the teachings of visual event detection to improve its utility in detecting a variety of events.

SUMMARY OF THE INVENTION

The invention provides methods and systems for automatic visual detection, recording, and retrieval of events. Herein
  an "event" corresponds to a specific condition, among some time-varying conditions within the field of view of an imaging device, that can be detected by visual means;
  "automatic visual detection" means that events are detected without need for human intervention or external trigger signals, based on the content of images captured by the imaging device;
  "recording" means that images corresponding to times before, during, and/or after the event are stored in a memory; and
  "retrieval" means that these images can be retrieved for purposes including display for a human user and further automated analysis by an image analysis system.

The methods and systems taught herein are useful for automatic visual detection of events for any purpose, including but not limited to signaling external equipment that an event has occurred and providing a synchronized output pulse that indicates when the event occurred. They are further useful for high-speed motion analysis of a mechanical process, and any other application for which images of short-duration, rare events are desired.

According to the teachings of the invention, a vision detector or other suitable device is placed so that its field of view includes some time-varying conditions, such as a mechanical process, wherein an event corresponding to some specific conditions may occur, and is configured to detect the events. The vision detector captures a sequence of frames, where each frame is an image of the field of view, and analyzes the frames using any of a variety of methods and systems, including but not limited to those taught in Vision Detector Method and Apparatus, and further detailed below, to obtain evidence that an event in the field of view has occurred.

When an event occurs the analysis will identify a set of event frames that together reveal sufficient evidence that the event has occurred. The set may contain just one event frame, and it may also contain a plurality of event frames. In the illustrative embodiments taught herein the event frames are consecutive in the sequence of frames, but it is straightforward to devise embodiments within the scope of the invention where the event frames are not strictly consecutive.

Consider the following example. The event to be detected corresponds to a moving mechanical component traveling outside a zone of acceptable tolerance. A vision detector is configured to detect the component in an error zone, a region of the field of view that is outside the acceptable zone. Suppose that on some machine cycle the component moves through the error zone for three consecutive frames. Suppose further that the analysis of the frames reveals strong evidence that the component is in the error zone for the first and third frames, but weak evidence that the component is in the error zone for the second frame. This may occur because the viewing perspective or position of the component relative to the illumination in the second frame is such that the component is difficult to see. The analysis also reveals that the component is unlikely to have been in the zone for many frames before and after the three critical frames.

The set of event frames began when the first frame revealed strong evidence that the event was occurring, and ended at the third frame when subsequent frames revealed no evidence that the event was continuing. The combined positive evidence of the first and third frames and weak evidence of the second frame is judged to be sufficient to conclude that the event has occurred. The three frames are the event frames in this example.

In some embodiments the second frame is not considered an event frame—the choice of whether or not to consider the second frame to be an event frame can be made either way within the scope of the invention. In the illustrative embodiments taught herein, the event frames are consecutive and would include the second frame When the evidence is judged to be sufficient to decide that an event has occurred, a plurality of selected frames are chosen from the sequence of frames to be recorded in a memory. A frame is chosen to be recorded depending on its position in the sequence of frames relative either to the event frames, or to a mark time computed as described herein. The event frames themselves may be recorded, frames prior to the event frames in the sequence may be recorded, and frames after the event frames in the sequence may be recorded. In an illustrative embodiment, frames captured within a user-specified time interval relative to the mark time are recorded. In another illustrative embodiment a predetermined number of frames are recorded, including the event frames and consecutive frames immediately prior to and immediately after the event frames.

Frames from these stored selected frames are retrieved in response to commands and used for various purposes, including display for a human user who is using a graphical user interface to issue the commands, and further automated image analysis by an image analysis system that is issuing the commands.

In embodiments where the frames are displayed for a human user, it is generally desirable to display several frames at once but typically not practical to display all of the recorded images at once at a display resolution sufficient for the user to see useful detail in each image. According to the invention a portion of the recorded frames are displayed at one time. The user chooses the portion to be displayed by issuing scrolling commands to advance the portion to be displayed forward or backward. The portion to be displayed at one time preferably includes several frames, but can include as few as one frame.

In an illustrative embodiment, the frames are displayed using a graphical user interface (GUI). The portion of frames displayed at one time are contained in a filmstrip window of the GUI, which displays the portion of frames as a succession of low-resolution "thumbnail" images. The resolution of the thumbnail images is chosen to be low enough that a useful number of images can been seen at one time, and high enough that each image is sufficiently detailed to be useful. The scrolling commands are provided by conventional GUI elements.

This illustrative embodiment further displays one frame of the portion of frames at full resolution in an image view window. As the scrolling commands advance the filmstrip forward and/or backward, the frame displayed in the image view window will also be advanced forward or backward.

In an illustrative embodiment, evidence that an event in the field of view has occurred is obtained for each frame in the form of a value, called an event detection weight, that indicates a level of confidence that the event is occurring or has occurred. The value may be a simple yes/no choice that indicates high or low confidence, a number that indicates a range of levels of confidence, or any item of information that conveys evidence. One example of such a number is a so-called fuzzy logic value, further described herein. Note that no machine can make a perfect decision from an image, and so will instead make judgments based on imperfect evidence.

An event detection weight is obtained for each frame by image analysis operations on one or more regions of interest in the frame. In an illustrative embodiment, each image analysis operation computes a measurement based on the pixel values in the region of interest, where the measurement is responsive to the amount, pattern, or other characteristic of light within the region. The measurement is converted to a logic value by a threshold operation, and the logic values obtained from the regions of interest are combined to produce the event detection weight for the frame. The logic values can be binary or fuzzy logic values, with the thresholds and logical combination being binary or fuzzy as appropriate.

In an illustrative embodiment, event frames are a set of consecutive frames for which:
  the event detection weight for the first and last frames in the set exceed a threshold;
  the last frame is followed by at least some predetermined number of frames where the event detection weight does not exceed the threshold; and
  the event detection weights of the set of frames satisfy some predetermined condition.

Any suitable condition can be defined for this purpose, which can depend on statistics including but not limited to:
  the number of frames in the set;
  the average (mean) event detection weight;
  the total event detection weight;
  the median event detection weight; and
  the number or fraction of frames in the set for which the event detection weight exceeds a threshold.

It is desirable that frames recorded according to the present invention be stamped with the time at which they were captured. To support detailed study of the event, it is most useful for the timestamps to be relative to the time of occurrence of the event itself, rather than, for example, time of day. The event frames define a broad range of times for the event, however, not a specific point in time. In order to obtain a specific and meaningful time for the event, one may use the mark time as taught in Vision Detector Method and Apparatus. As taught therein, mark time is the time at which an object crosses some fixed, imaginary reference point, which can be computed accurately following those teachings.

Not all events correspond to an object crossing a reference point, however. In some cases, for example, the event may correspond to a stroke motion, wherein a mechanical component advances and then retreats within the field of view. In such cases the mark time would more usefully be defined as the apex of the stroke, rather than the crossing of a reference point. Motion across a reference point will be called a flow event, and motion of advance and retreat will be called a stroke event. The present invention includes methods and systems for selecting between flow and stroke events, and computing mark time for stroke events (mark time for flow events was taught in Vision Detector Method and Apparatus).

Event detection according to the present invention is an example of visual event detection as taught in Vision Detector Method and Apparatus, which states: "The method of visual event detection involves capturing a sequence of frames and analyzing each frame to determine evidence that an event is occurring or has occurred." As taught therein visual event detection was primarily directed towards embodiments where the events to be detected corresponded to discrete objects passing through the field of view, and where it was generally desirable to inspect those objects. The reader will note the strong similarity between object detection weights and object pass scores taught therein, and event detection weights used in the present invention. Indeed any method or apparatus taught therein for obtaining an object detection weight or object pass score can be used to obtain an event detection weight, the only difference being the purpose for which these weights and scores are intended, and not the manner in which they are obtained.

Furthermore, detecting that an object has passed through the field of view, or more particularly that a defective object has passed through the field of view, is an example of an event for which it may be desirable to detect, record, and retrieve according to the present invention. Indeed there is little difference between detecting an object passing through the field of view and detecting a mechanical component entering an error zone as in the above example. Thus the teachings of Vision Detector Method and Apparatus may generally be considered illustrative embodiments of the present invention, where recording and retrieval methods and systems, and improved event detection methods and systems, would be added as taught herein.

BRIEF DESCRIPTION OF THE DRAWINGS

The invention will be more fully understood from the following detailed description, in conjunction with the accompanying figures, wherein.

DETAILED DESCRIPTION OF THE INVENTION

Basic Operation of the Invention

Figure 1:
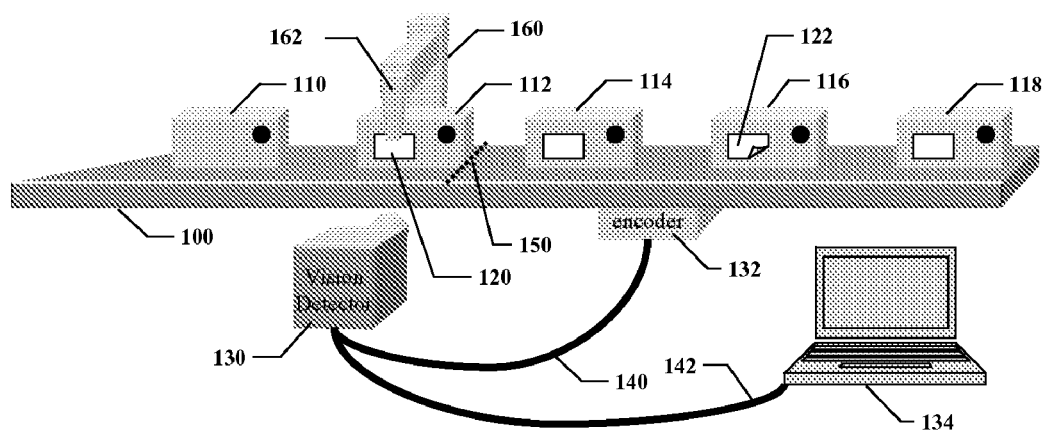
FIG. 1 shows an illustrative embodiment of a system for detecting, recording, and retrieving visual events according to the present invention, wherein the events correspond to applying defective labels on objects moving on a production line.

FIG. 1 shows an illustrative embodiment of a vision detector configured to detect certain events that may occur on a production line, and to record and retrieve images of those events. A conveyer 100 transports objects, including example objects 110, 112, 114, 116, and 118, left to right past a labeling mechanism 160, which acts to place a label on each object, for example label 120 on object 112. The labeling mechanism 160 includes an arm 162 that acts so as to move and apply each label to each object. Note that labeling mechanism 160 and arm 162 are shown for illustrative purposes to explain the invention, and do not necessarily represent any particular mechanism used to apply labels in industrial production.

The labeling mechanism 160 may occasionally malfunction, resulting for example in the misapplied label 122, whose lower right corner is bent away from the surface of object 116. Many industrial productions lines will use some form of automatic optoelectronic inspection, such as a set of photodetectors, a machine vision system, or a vision detector, to detect and reject defective object 116. While such inspection is valuable in preventing defective objects from reaching customers, it does nothing to prevent defects from being made in the first place. One objective of the present invention is to aid manufacturing engineers in diagnosing and fixing the cause of defective objects by providing images that show the defect actually being created.

In addition to transporting objects for production purposes, conveyer 100 causes relative movement between the objects and the field of a view of vision detector 130. On many production lines motion of the conveyer is tracked by a shaft encoder 132, which produces a signal 140 that can be received by vision detector 130 and used for various purposes as taught in Vision Detector Method and Apparatus and herein. For example, the signal 140 can be used by the vision detector 130 as a reference to the point in time that object 112 crosses an imaginary reference point 150, called the mark point.

Vision detector 130 detects certain events that may occur in its field of view, based on appropriate visual criteria. In the illustrative embodiment of FIG. 1, an event would correspond to the misapplication of a label by arm 162, which can be detected in various ways as further described below. Images are recorded at times before, during, and after the event. A human user, such as a manufacturing engineer or technician, would interact with a Human-Machine Interface 134 via signal 142 to retrieve the recorded images so that the mechanical problems leading to misapplied labels could be diagnosed.

In another embodiment there are no discrete objects, but rather material flows past the vision detector continuously, for example on a web, an example of which is provided below. For purposes of event detection, recording, and retrieval, there is little difference between discrete objects and continuous flow of material.

Figure 2:
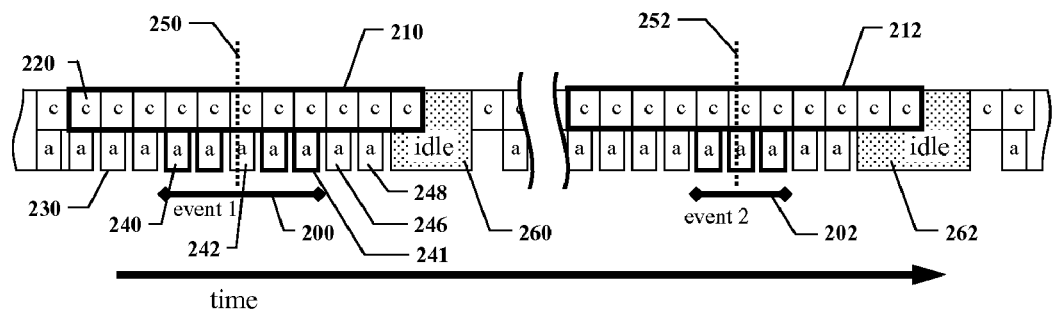
FIG. 2 shows a timeline that illustrates a typical operating cycle for a system detecting events according to the invention.

FIG. 2 shows a timeline that illustrates a typical operating cycle for a vision detector configured to detect events and record images. Boxes labeled "c", such as box 220, represent image capture. Boxes labeled "a", such as box 230, represent analysis (analysis steps are further subdivided and described below). It is desirable that capture "c" of the next image be overlapped with analysis "a" of the current image, so that (for example) analysis step 230 analyzes the image captured in capture step 220. In this timeline, analysis is shown as taking less time than capture, but in general analysis will be shorter or longer than capture depending on the application details.

If capture and analysis are overlapped, the rate at which a vision detector can capture and analyze images is determined by the longer of the capture time and the analysis time. This is the "frame rate".

A portion 200 of the timeline corresponds to a first event, and includes the capture and analysis of five event frames. A second portion 202 corresponds to a second event, and includes three event frames.

In illustrative embodiments considered herein, analysis of the captured images for event detection includes three principal subdivisions:

a visual analysis step to evaluate evidence that an event is occurring or has occurred in an individual frame;

an activity analysis step to identify a set of consecutive frames, called candidate frames, for which an event to be detected may be occurring; and an event analysis step to determine whether or not an event to be detected has occurred in a set of candidate frames.

Each visual analysis step considers the evidence that an event is occurring in an individual frame. Frames where the evidence is strong are called active. Analysis steps for active frames are shown with a thick border, for example analysis step 240. In illustrative embodiments considered herein, this evidence is represented by a fuzzy logic value called an event detection weight (further described below), which is computed by image analysis operations of one or more regions of interest in the frame as taught below and in Vision Detector Method and Apparatus.

Each activity analysis step considers the evidence that an event is occurring or has occurred within a recent set of frames. In illustrative embodiments considered herein, event detection is considered to be in either an active state, signifying that there is some evidence that an event is occurring, or an inactive state, indicating that there is little such evidence. One function of the activity step is to determine this state. In an illustrative embodiment, a transition from the inactive state to the active state is made when an active frame is found. A transition from the active state to the inactive state is made when some number of consecutive inactive frames are found. The candidate frames include the consecutive set of frames beginning with the first active frame and ending with the last active frame, and may include inactive frames in between. Another function of the activity analysis steps is to gather statistics describing the set of candidate frames.

Each event analysis step then considers evidence that an event has occurred during the candidate frames by examining the evidence gathered by preceding activity analysis steps. In illustrative embodiments considered herein, an event analysis step is performed whenever a transition from the active state to the inactive state is made. The statistics describing the candidate frames are examined, and if they reveal sufficient evidence to conclude that an event has occurred, the candidate frames are considered event frames. Recording and other appropriate actions as further described below are performed.

A variety of methods may be used perform visual, activity, and event analysis within the scope of the invention; some are described below and in Vision Detector Method and Apparatus, and many others will occur to those skilled in the art.

In the example of FIG. 2, event detection for first event 200 enters the active state with the first active frame corresponding to analysis step 240, and ends with two consecutive inactive frames, corresponding to analysis steps 246 and 248. Note that for the first event, a single inactive frame corresponding to analysis step 242 is not sufficient to enter the inactive state.

When the inactive state is entered, for example at the end of analysis step 248, an event analysis step is performed. The candidate frames are the five event frames starting with analysis step 240 and ending with analysis step 241. In this example the event analysis step concludes that an event has occurred, and causes the recording of a first set of recorded frames 210. A similar analysis for second event 202 results in recording of a second set of recorded frames 212.

By considering the position of the object in the active frames as it passes through the field of view, as further described below, the vision detector estimates mark times 250 and 252, which represent precise times at which the events have occurred. A timestamp is stored for each recorded frame indicating the relative time between the mark time and the midpoint of the shutter time corresponding to each such recorded frame.

Once a transition to the inactive state is made, the vision detector may enter an idle step, for example first idle step 260 and second idle step 262. Such a step is optional, but may be desirable for several reasons. If a minimum time between events is known, there is no need to be looking for an event until just before a new one might happen. An idle step will eliminate the chance of false event detection at times when an event couldn't happen, and will extend the lifetime of the illumination system because the lights can be kept off during the idle step.

Figure 3:
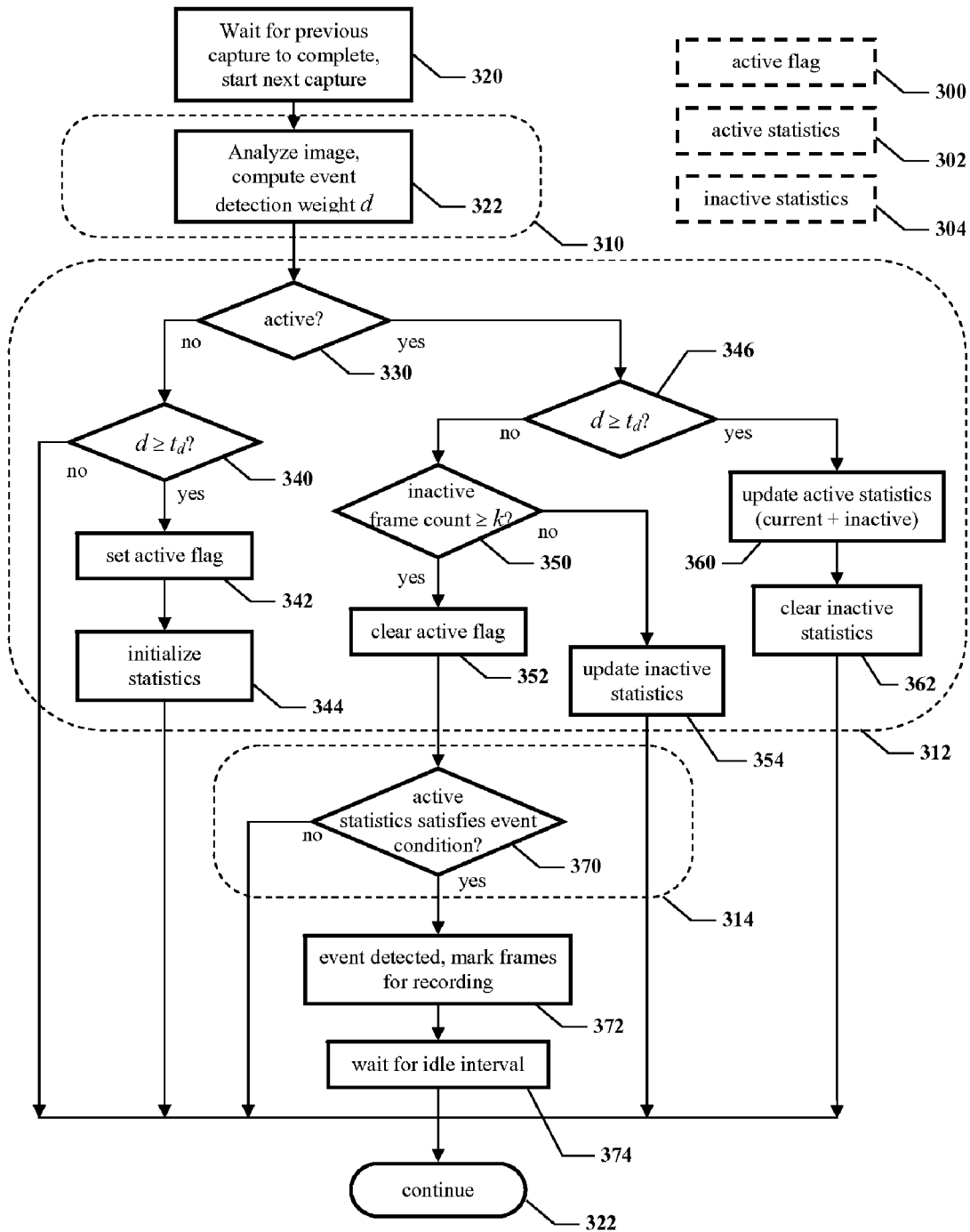
FIG. 3 shows a flowchart that describes analysis steps performed by an illustrative embodiment.

FIG. 3 shows a flowchart that provides details of the analysis steps of event detection. Boxes with a dashed border represent data used by the flowchart. Rounded rectangles enclosing flowchart blocks show the analysis subdivisions, including visual analysis step 310, activity analysis step 312, and event analysis step 314.

Active flag 300 holds the active/inactive state used by the activity analysis steps.

Statistics gathered by the activity analysis steps are held in active statistics 302 and inactive statistics 304. Values for active frames are added directly to active statistics 302. For an inactive frame, the activity analysis step does not yet know whether the frame will be part of the set of candidate frames—that depends on the status of future frames. Thus values for inactive frames are added to inactive statistics 304. If an active frame is subsequently found before a transition to the inactive state is made, inactive statistics 304 are added to active statistics 302 and cleared. Inactive statistics 304 remaining at the time of a transition to the inactive state are discarded. Both statistics include a count of the number of frames that have been added.

In the illustrative embodiment of FIG. 3, the flowchart is executed repeatedly, once for each frame, from capture block 320 through continue block 324. Capture block 320 synchronizes the analysis with the frame capture and provides for capture of the next frame to be overlapped with analysis of the current frame. Visual analysis block 322 performs the visual analysis step, computing an event detection weight d from an analysis of the captured image.

Activity analysis step 312 is performed next. Active block 330 tests active flag 300 to determine the current state of event detection. If event detection is inactive, first threshold block 340 determines the active/inactive status of the current frame by comparing d to a threshold $t_d$. If the event detection weight d is not greater than the threshold $t_d$, the frame is inactive, and activity analysis ends for the current frame. If the event detection weight d is greater than the threshold $t_d$, the frame is active, active transition block 342 sets active flag 300, and initialize block 344 initializes active statistics 302 using values from the current frame, and clears inactive statistics 304.

If active block 330 determines that the current state is active, then second threshold block 346 determines the active/inactive status of the current frame by comparing d to a threshold $t_d$. If d is not greater than the threshold, then the frame is inactive, and count test block 350 looks at the frame count in inactive statistics 304 to determine whether more than a parameter k of consecutive inactive frames have been found. If not, inactive update block 354 updates inactive statistics 304 by adding values from the current frame (including incrementing the frame count). If so, inactive transition block 352 clears active flag 300 and execution continues with event analysis step 314.

If second threshold block 346 determines that the current frame is active, then active update block 360 updates active statistics 302 by adding values from both the current frame and inactive statistics 304. Clear block 362 then clears inactive statistics 304

If activity analysis step 312 makes a transition from the active state to the inactive state, then event analysis step 314 is performed. Condition block 370 tests active statistics 302 to determine whether an event has occurred. If not, gather statistics are ignored and execution continues. If so, event block 372 marks frames for recording, as further described below. Idle block 374 waits for an idle interval before continuing.

Figures 4, 5:
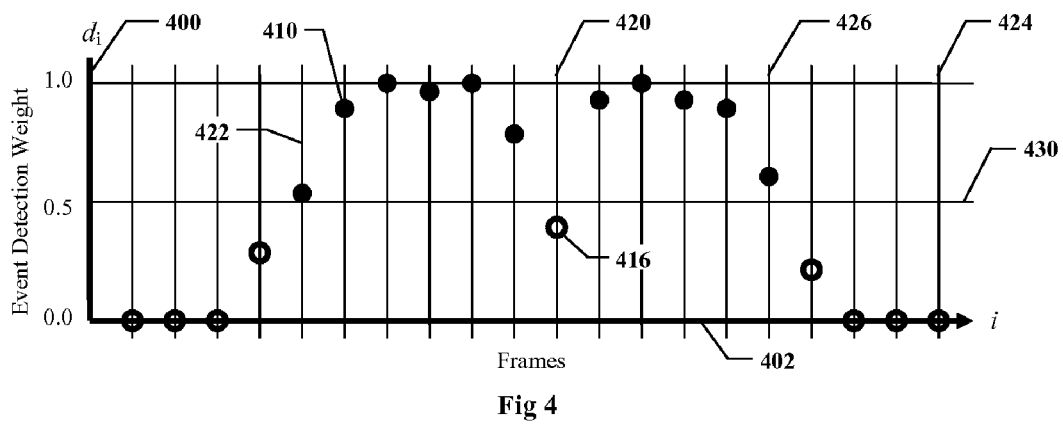
FIG. 4 illustrates how evidence is weighed for visual event detection in an illustrative embodiment.
FIG. 5 shows statistics that are gathered and used for event detection in an illustrative embodiment.

FIG. 4 further illustrates the analysis steps of an illustrative embodiment, and can be used in conjunction with the timeline of FIG. 2 and the flowchart of FIG. 3 to understand the basic operation of the invention.

FIG. 4 illustrates how evidence is weighed for event detection in an illustrative embodiment. As discussed above, information comprising evidence that an event is occurring or has occurred in the field of view is called an event detection weight. The figure shows a plot of event detection weights $d_i$ on vertical axis 400 versus frame count i on horizontal axis 402. Each frame is represented by a vertical line, such as example line 426. Note that the frame count is an arbitrary integer.

In this embodiment $d_i$ is a fuzzy logic value representing evidence that an event is occurring in frame i, and is computed by the vision detector on each frame using methods further described below and in Vision Detector Method and Apparatus.

In the illustrative embodiment of FIG. 4, event detection threshold $t_d$ is 0.5, so that frames where $d_i \geq 0.5$ are considered active frames. For reference, a line 430 where $d_i=0.5$ is plotted. Event detection weights for active frames are plotted as solid circles, for example point 410, and those for inactive frames are plotted as open circles, for example point 416.

In the example of FIG. 4, event detection enters the active state on frame 422, and enters the inactive state after frame 424, when four consecutive inactive frames have been seen (inactive frame count threshold k=3 in this example). The set of candidate frames starts with frame 422 and ends with frame 426. The isolated inactive frame 420 does not cause a transition to the inactive state.

FIG. 5 gives details of statistics gathered by activity analysis step 312 and used by event analysis step 314 in an illustrative embodiment, and also for the example of FIG. 4. For this embodiment, active statistics 302 and inactive statistics 304 would include sufficient information to compute these statistics when a transition to the inactive state is made. Each statistic in FIG. 5 includes a symbol 500, further described below, a description 510 that serves to define the value, and an example 520 that shows what the value would be for the example of FIG. 4.

The above descriptions of methods for weighing evidence to determine whether an event has been detected are intended as examples of useful embodiments, but do not limit the methods that can be used within the scope of the invention. For example, the exemplary constants $t_d$=0.5 used above may be replaced with any suitable value. Many additional methods for visual event detection will occur to those skilled in the art.

Illustrative Apparatus

Figure 6:
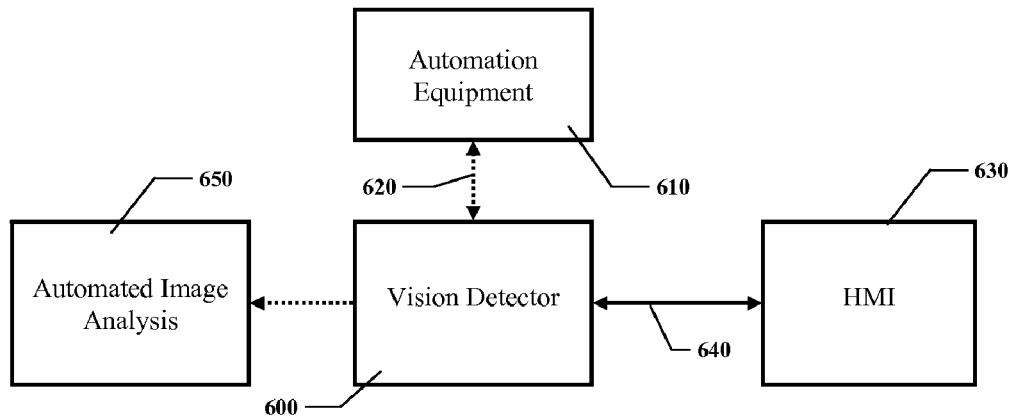
FIG. 6 shows a high-level block diagram for a system according to the invention.

FIG. 6 shows a high-level block diagram for a vision detector used for visual detection, recording, and retrieval of events. A vision detector 600 may be connected to appropriate automation equipment 610, which may include PLCs, reject actuators, shaft encoders, and/or photodetectors, by means of signals 620. These connections are not required for detection, recording, and retrieval of events, but may be useful in cases where it is desirable to use the vision detector for additional purposes, for example those taught in Vision Detector Method and Apparatus. It may be particularly desirable, for example, to provide an output pulse to signal that an event has been detected. Such as pulse would be delayed and synchronized to a mark time as taught in Vision Detector Method and Apparatus, and used by a PLC, actuator, or other device.

For retrieval display of images of detected events, the vision detector is connected to a human-machine interface (HMI) 630, such as a PC or hand-held device, by means of signals 640. HMI 630 is also used for setup. HMI 630 need not be connected for detection and recording of events, but must of course be reconnected for retrieval and display. Signals 640 can be implemented in any acceptable format and/or protocol and transmitted in a wired or wireless form.

Images of events recorded by vision detector 600 may also be retrieved by an automated image analysis system 650, including but not limited to a conventional machine vision system. Such a system might be used to make a more sophisticated analysis of the images than might be possible with a vision detector designed to operate at very high frame rates, but without requiring the human analysis inherent in the use of HMI 630.

Figure 7:
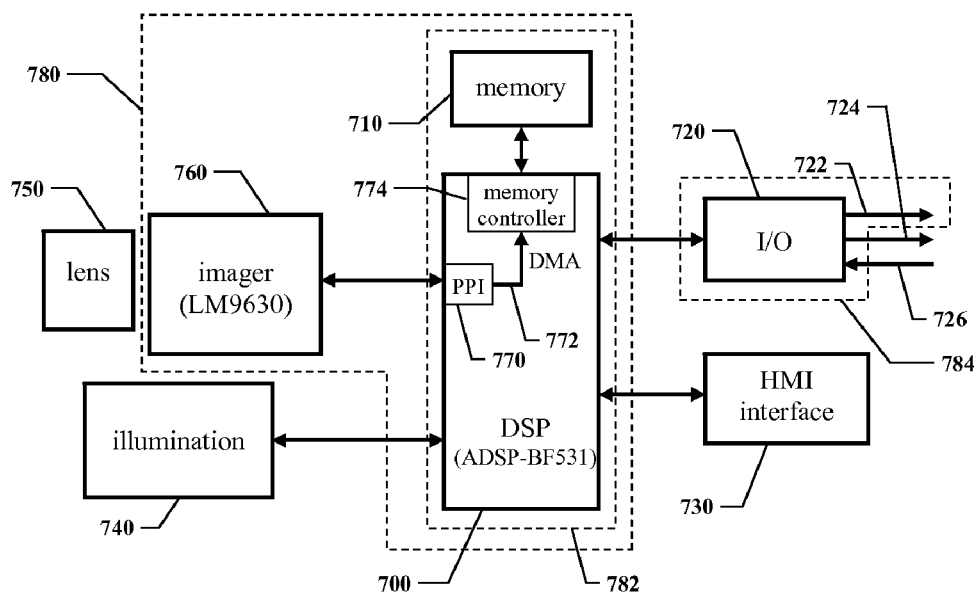
FIG. 7 shows a block diagram of an illustrative embodiment of a vision detector that can use used as part of a system according to the invention.

FIG. 7 shows a block diagram of an illustrative embodiment of a vision detector that might be used to practice the invention. A digital signal processor (DSP) 700 runs software to control capture, analysis, recording, HMI communications, and any other appropriate functions needed by the vision detector. The DSP 700 is interfaced to a memory 710, which includes high speed random access memory for programs and data and non-volatile memory to hold programs and setup information when power is removed. The memory 710 also holds recorded images for subsequent retrieval. The DSP is also connected to an I/O module 720 that provides signals to automation equipment, an HMI interface 730, an illumination module 740, and an imager 760. A lens 750 focuses images onto the photosensitive elements of the imager 760.

The DSP 700 can be any device capable of digital computation, information storage, and interface to other digital elements, including but not limited to a general-purpose computer, a PLC, or a microprocessor. It is desirable that the DSP 700 be inexpensive but fast enough to handle a high frame rate. It is further desirable that it be capable of receiving and storing pixel data from the imager simultaneously with image analysis.

In the illustrative embodiment of FIG. 7, the DSP 700 is an ADSP-BF531 manufactured by Analog Devices of Norwood, Mass. The Parallel Peripheral Interface (PPI) 770 of the ADSP-BF531 DSP 700 receives pixel data from the imager 760, and sends the data to memory controller 774 via Direct Memory Access (DMA) channel 772 for storage in memory 710. The use of the PPI 770 and DMA 772 allows, under appropriate software control, image capture to occur simultaneously with any other analysis performed by the DSP 700. Software instructions to control the PPI 770 and DMA 772 can be implemented by one of ordinary skill in the art following the programming instructions contained in the ADSP-BF533 Blackfin Processor Hardware Reference (part number 82-002005-01), and the Blackfin Processor Instruction Set Reference (part number 82-000410-14), both incorporated herein by reference. Note that the ADSP-BF531, and the compatible ADSP-BF532 and ADSP-BF533 devices, have identical programming instructions and can be used interchangeably in this illustrative embodiment to obtain an appropriate price/performance tradeoff.

The high frame rate desired by a vision detector suggests the use of an imager unlike those that have been used in prior art vision systems. It is desirable that the imager be unusually light sensitive, so that it can operate with extremely short shutter times using inexpensive illumination. It is further desirable that it be able to digitize and transmit pixel data to the DSP far faster than prior art vision systems. It is moreover desirable that it be inexpensive and have a global shutter.

These objectives may be met by choosing an imager with much higher light sensitivity and lower resolution than those used by prior art vision systems. In the illustrative embodiment of FIG. 7, the imager 760 is an LM9630 manufactured by National Semiconductor of Santa Clara, Calif. The LM9630 has an array of 128 by 100 pixels, for a total of 12800, about 24 times fewer than typical prior art vision systems. The pixels are relatively large at 20 microns square, providing high light sensitivity. The LM9630 can provide 500 frames per second when set for a 300 microsecond shutter time, and is sensitive enough (in most cases) to allow a 300 microsecond shutter using LED illumination. This resolution would be considered far too low for a vision system, but is quite sufficient for the feature detection tasks that are the objectives of the Vision Detector Method and Apparatus. Electrical interface and software control of the LM9630 can be implemented by one of ordinary skill in the art following the instructions contained in the LM9630 Data Sheet, Rev 1.0, January 2004, which is incorporated herein by reference.

It is desirable that the illumination 740 be inexpensive and yet bright enough to allow short shutter times. In an illustrative embodiment, a bank of high-intensity red LEDs operating at 630 nanometers is used, for example the HLMP-ED25 manufactured by Agilent Technologies. In another embodiment, high-intensity white LEDs are used to implement desired illumination.

In the illustrative embodiment of FIG. 7, the I/O module 720 provides output signals 722 and 724, and input signal 726. Input signal 726 can be used for event detection by appropriate connections in a logic view as taught in Vision Detector Method and Apparatus.

As used herein an image capture device provides means to capture and store a digital image. In the illustrative embodiment of FIG. 7, image capture device 780 comprises a DSP 700, imager 760, memory 710, and associated electrical interfaces and software instructions.

As used herein an analyzer provides means for analysis of digital data, including but not limited to a digital image. In the illustrative embodiment of FIG. 7, analyzer 782 comprises a DSP 700, a memory 710, and associated electrical interfaces and software instructions.

As used herein an output signaler provides means to produce an output signal responsive to an analysis. In the illustrative embodiment of FIG. 7, output signaler 784 comprises an I/O module 720 and an output signal 722.

As used herein a process refers to systematic set of actions directed to some purpose, carried out by any suitable apparatus, including but not limited to a mechanism, device, component, software, or firmware, or any combination thereof that work together in one location or a variety of locations to carry out the intended actions.

In an illustrative embodiment, various processes used by the present invention are carried out by an interacting collection of digital hardware elements and computer software instructions. These hardware elements include DSP 700, which provides general-purpose information processing actions under control of suitable computer software instructions;

memory 710, which provides storage and retrieval actions for images, data, and computer software instructions;

imager 760, which provides, in combination with other elements as described herein, image capture actions;

I/O module 720, which provides interface and signaling actions; and

HMI interface 730, which provides human-machine interface actions.

Figure 8:
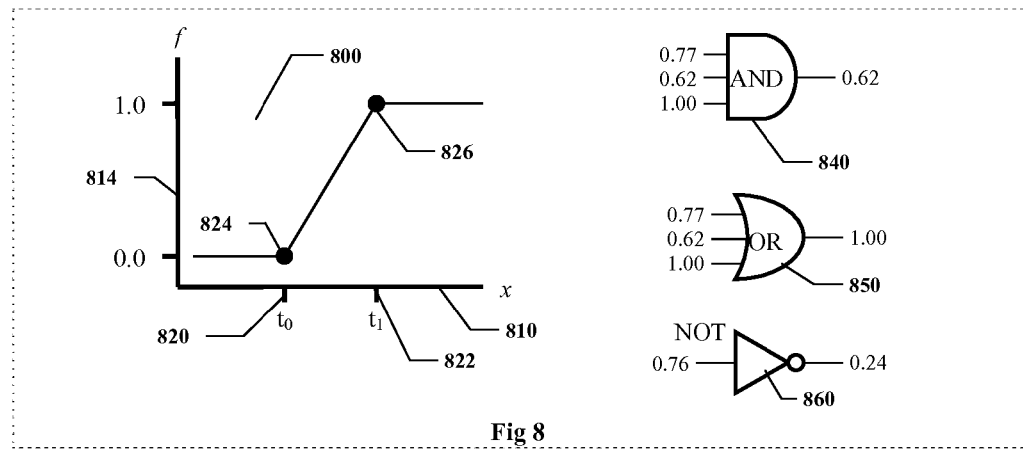
FIG. 8 shows fuzzy logic elements used in an illustrative embodiment to weigh evidence and make judgments, including judging whether an object is present and whether it passes inspection.
Figure 9:
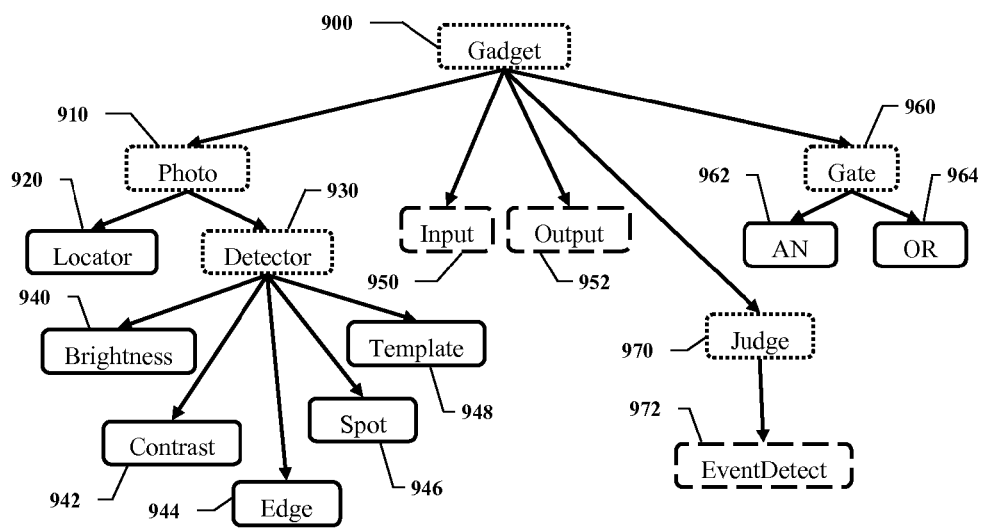
FIG. 9 shows the organization of a set of software elements (e.g., program instructions of a computer readable medium) used by an illustrative embodiment to analyze frames, make judgments, sense inputs, and control output signals.
Figure 10:
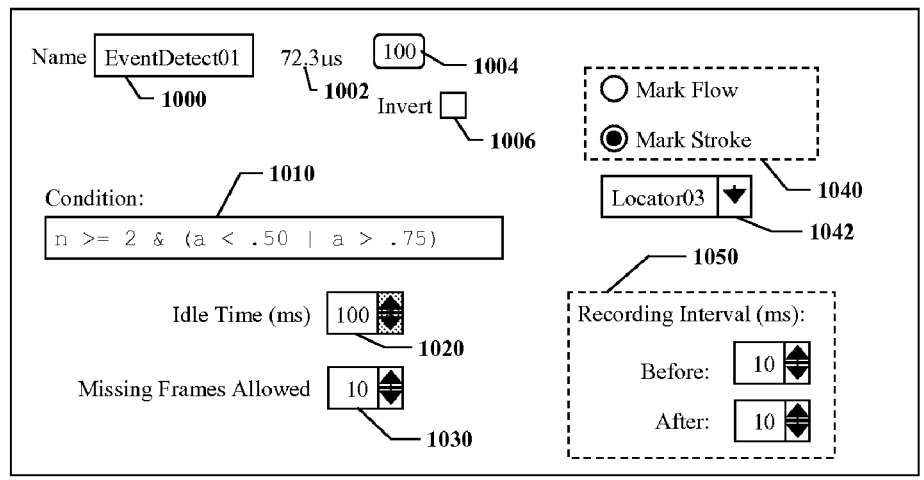
FIG. 10 shows a portion of an HMI for user configuration of event detection parameters, which will be used to further describe an illustrative embodiment of visual event detection.
Figure 20:
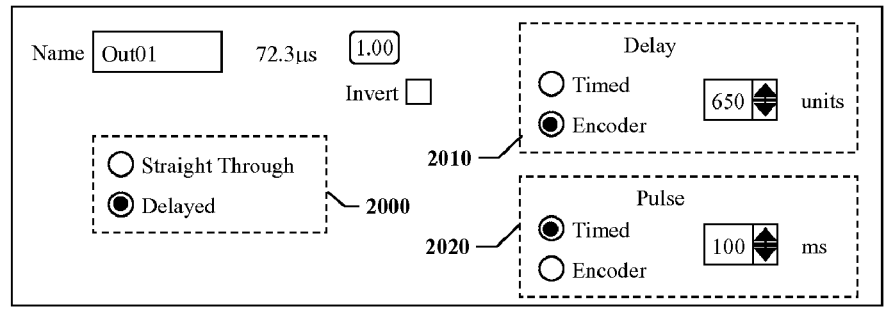
FIG. 20 shows a portion of the HMI for user configuration of output signals.

In an illustrative embodiment the computer software instructions include those for carrying out the actions described herein for the flowchart steps of FIG. 3, which describes portions of illustrative capture and analysis processes;

the fuzzy logic elements of FIG. 8, which describes illustrative decision logic;

the software elements of FIG. 9, which illustrates a set of software elements that can be used to practice the invention; and the graphical controls of FIGS. 10 and 20, which illustrate how human users can select operating parameters.

Furthermore, it will be understood by those skilled in the art that the above is a list of examples only. It is not exhaustive, and suitable computer software instructions may be used in illustrative embodiments to carry out processes used for any figure described herein.

Examples of processes described herein include:

- a capture process, comprising capture block 320 (FIG. 3), and other actions as described herein, and carried out by image capture device 780;
- a variety of analysis processes, comprising portions of FIG. 3, for example visual analysis step 310, activity analysis step 312, and event analysis step 314, and other actions as described herein, and carried out by analyzer 782 and suitable software elements shown in FIG. 9;
- a variety of selection processes, comprising for example event block 372, and other actions as described herein, and carried out by analyzer 782 and suitable software elements shown in FIG. 9; and
- a variety of decision processes, comprising for example condition block 370, and other actions as described herein, and carried out by analyzer 782 and suitable software elements shown in FIG. 9.

It will be understood by one of ordinary skill that there are many alternate arrangements, devices, and software instructions that could be used within the scope of the invention to implement an image capture device 780, analyzer 782, and output signaler 784. Similarly, many alternate arrangements, devices, and software instructions could be used within the scope of the invention to carry out the processes described herein.

Fuzzy Logic Decision Making

FIG. 8 shows fuzzy logic elements used in an illustrative embodiment to weigh evidence and make judgments, including judging whether an event is occurring or has occurred.

A fuzzy logic value is a number between 0 and 1 that represents an estimate of confidence that some specific condition is true. A value of 1 signifies high confidence that the condition is true, 0 signifies high confidence that the condition is false, and intermediate values signify intermediate levels of confidence.

The more familiar binary logic is a subset of fuzzy logic, where the confidence values are restricted to just 0 and 1. Therefore, any embodiment described herein that uses fuzzy logic values can use as an alternative binary logic values, with any fuzzy logic method or apparatus using those values replaced with an equivalent binary logic method or apparatus.

Just as binary logic values are obtained from raw measurements by using a threshold, fuzzy logic values are obtained using a fuzzy threshold. Referring to FIG. 8, a graph 800 illustrates a fuzzy threshold. The x-axis 810 represents a raw measurement, and the $f$-axis 814 represents the fuzzy logic value, which is a function whose domain includes all possible raw measurements and whose range is $0 \leq f \leq 1$.

In an illustrative embodiment, a fuzzy threshold comprises two numbers shown on the x-axis, low threshold $t_0$ 820, and high threshold $t_1$ 822, corresponding to points on the function 824 and 826. The fuzzy threshold can be defined by the equation $$f = \min\left(\max\left(\frac{x - t_0}{t_1 - t_0}, 0\right), 1\right) \quad (1)$$

Note that this function works just as well when $t_1 < t_0$. Other functions can also be used for a fuzzy threshold, such as the sigmoid $$f = \frac{1}{1 + e^{-(x-t)/\sigma}} \quad (2)$$

where $t$ and $\sigma$ are threshold parameters. In embodiments where simplicity is a goal, a conventional binary threshold can be used, resulting in binary logic values.

Fuzzy decision making is based on fuzzy versions of AND 840, OR 850, and NOT 860. A fuzzy AND of two or more fuzzy logic values is the minimum value, and a fuzzy OR is the maximum value. Fuzzy NOT of f is 1−f. Fuzzy logic is identical to binary when the fuzzy logic values are restricted to 0 and 1.

In an illustrative embodiment, whenever a hard true/false decision is needed, a fuzzy logic value is considered true if it is at least 0.5, false if it is less than 0.5.

It will be clear to one skilled in the art that there is nothing critical about the values 0 and 1 as used in connection with fuzzy logic herein. Any number could be used to represent high confidence that a condition is true, and any different number could be used to represent high confidence that the condition is false, with intermediate values representing intermediate levels of confidence.

Software Elements of the Invention

FIG. 9 shows the organization of a set of software elements (e.g., program instructions of a computer readable medium) used by an illustrative embodiment to analyze frames, make judgments, sense inputs, and control output signals. The elements may be implemented using a class hierarchy in a conventional object-oriented programming language such as C++, so that each of the elements corresponds to a class. However, any acceptable programming technique and/or language can be used to carry out the processes described herein.

As illustrated, classes with a dotted border, such as Gadget class 900, are abstract base classes that do not exist by themselves but are used to build concrete derived classes such as Locator class 920. Classes with a solid border represent dynamic objects that can be created and destroyed as needed by the user in setting up an application, using an HMI 630. Classes with a dashed border, such as Input class 950, represent static objects associated with specific hardware or software resources. Static objects always exist and cannot be created or destroyed by the user.

All classes are derived from Gadget class 900, and so all objects that are instances of the classes shown in FIG. 9 are a kind of Gadget. In an illustrative embodiment, every Gadget:

1. has a name that can be chosen by the user;
2. has a logic output (a fuzzy logic value) that can be used as a logic input by other gadgets to make judgments and control output signals;
3. has a set of parameters than can be configured by a user to specify its operation;
4. has one such parameter that can be used to invert the logic output (i.e. fuzzy NOT); and
5. can be run, which causes its logic output to be updated based on its parameters, logic inputs if any, and for certain Gadgets the contents of the current frame, and which may also cause side-effects such as the setting of an output signal.

The act of analyzing a frame consists of running each Gadget once, in an order determined to guarantee that all logic inputs to a Gadget have been updated before the Gadget is run. In some embodiments, a Gadget is not run during a frame where its logic output is not needed.

The Photo class 910 is the base class for all Gadgets whose logic output depends on the contents of the current frame.

These are the classes that actually do the image analysis. Every Photo measures some characteristic of a region of interest (ROI) of the current frame. The ROI corresponds to a visible feature on the object to be inspected. This measurement is called the Photo's analog output. The Photo's logic output is computed from the analog output by means of a fuzzy threshold, called the sensitivity threshold, that is among its set of parameters that can be configured by a user. The logic output of a Photo can be used to provide evidence to be used in making judgments.

The Detector class 930 is the base class for Photos whose primary purpose is to make measurements in an ROI and provide evidence to be used in making judgments. In an illustrative embodiment all Detector ROIs are circles. A circular ROI simplifies the implementation because there is no need to deal with rotation, and having only one ROI shape simplifies what the user has to learn. Detector parameters include the position and diameter of the ROI.

A Brightness Detector 940 measures a weighted average or percentile brightness in the ROI. A Contrast Detector 942 measures contrast in the ROI. An Edge Detector 944 measures the extent to which the ROI looks like an edge in a specific direction. A Spot Detector 946 measures the extent to which the ROI looks like a round feature such as a hole. A Template Detector 948 measures the extent to which the ROI looks like a pre-trained pattern selected by a user. The operation of the Detectors is further described in Vision Detector Method and Apparatus.

The Locator class 920 represents Photos that have two primary purposes. The first is to produce a logic output that can provide evidence for making judgments, and in this they can be used like any Detector. The second is to determine the location of an object in the field of view of a vision detector, so that the position of the ROI of other Photos can be moved so as to track the position of the object. Any Locator can be used for either or both purposes.

In an illustrative embodiment, a Locator searches a one-dimensional range in a frame for an edge. The search direction is normal to the edge, and is among the parameters to be configured by the user. The analog output of a Locator is similar to that for an Edge Detector. Locators are further described in Vision Detector Method and Apparatus.

In other embodiments, a Locator searches a multi-dimensional search range, using well-known methods, that may include translation, rotation, and size degrees of freedom. Suitable methods include those based on normalized correlation, the generalized Hough transform, and geometric pattern patching, all of which are well-known in the art and have been commercially available for many years. An illustrative embodiment of a multi-dimensional locator is provided in co-pending U.S. patent application Ser. No. 10/979,535, entitled METHOD FOR SETTING PARAMETERS OF A VISION DETECTOR USING PRODUCTION LINE INFORMATION, by Brian Mirtich and William M. Silver, filed Nov. 2, 2004, the teachings of which are expressly incorporated herein by reference The Input class 950 represents input signals to the vision detector, which can be used to influence event detection. The Output class 952 represents output signals from the vision detector, such as might be used to inform a PLC or actuator that an event has been detected. In the illustrative embodiment there is one static instance of the Input class for each physical input, such as exemplary input signal 726 (FIG. 7), and one static instance of the Output class for each physical output, such as exemplary output signals 722 and 724. An Output can produce delayed pulses synchronized to the mark time, as taught in Vision Detector Method and Apparatus, so that external automation equipment can determine when, using delay times, or where, using encoder counts, the event occurred.

The Gate base class 960 implements fuzzy logic decision making. Each Gate has one or more logic inputs than can be connected to the logic outputs of other Gadgets. Each logic input can be inverted (fuzzy NOT) by means of a parameter that a user can configure. An AND Gate 962 implements a fuzzy AND operation, and an OR Gate 964 implements a fuzzy OR operation.

The Judge class 970 is the base class for objects that weigh evidence over successive frames to make decisions. An illustrative embodiment of the present invention includes the EventDetect Judge 972, whose purpose is to implement activity analysis step 312 and event analysis step 314 (visual analysis step 310 is performed by some combination of Photos, Inputs, and/or Gates, with examples given below). Other types of Judges are taught in Vision Detector Method and Apparatus, and by be present in embodiment where it is desirable to combine functions provided therein with event detection as provided herein.

Each Judge has a logic input to which a user connects the logic output of a Photo or, more typically, a Gate that provides a logical combination of Gadgets, usually Photos and other Gates. The logic input to the EventDetect Judge provides the event detection weight for each frame. It is expressly contemplated that embodiments of the invention may use more than one EventDetect Judge, an example of which will be given below.

The logic output of the EventDetect Judge provides a pulse that indicates when an event has been detected. The leading edge of the pulse occurs when event analysis step 314 detects an event, for example at the end of analysis step 248 in FIG. 2, and the trailing edge occurs some time after that, for example at the end of idle step 260.

FIG. 10 shows graphical controls that can be displayed on an HMI for a user to view and manipulate in order to set parameters for an EventDetect Judge. A set of graphical controls displayed on HMI 630 for setting Gadget parameters is called a parameter view.

Name text box 1000 allows a user to view and enter a name for this EventDetect Judge. Time label 1002 shows the time taken by the most recent run of this EventDetect Judge. Logic output label 1004 shows the current logic output value of this EventDetect Judge, and may change color, shape, or other characteristic to distinguish between true ($\geq 0.5$) and false ($<0.5$). Invert checkbox 1006 allows the logic output of this EventDetect Judge to be inverted. Note that name text box 1000, time label 1002, logic output label 1004, and invert checkbox 1006 are common to the parameter views for all Gadget types, as further explained in Vision Detector Method and Apparatus.

Idle time spinner 1020 allows a user to specify the time interval for idle step 260 (FIG. 2), also shown as idle block 374 in FIG. 3.

Missing frame spinner 1030 allows a user to specify the maximum number of consecutive inactive frames that will be accepted without activity analysis step 312 making a transition to the inactive state. The value specified by missing frame spinner 1030 is used for the parameter k in count test block 350 of FIG. 3.

Marking control 1040 allows a user to select between flow and stroke events for computing mark time, as further described herein. To compute mark time the user must specify a Locator using locator list control 1042.

Recording interval controls 1050 allow the user to specify the time interval within which images are recorded when an event is detected, relative to the mark time. In an alternate embodiment, not shown, the user specifies whether or not to record the event frames, and the number of frames before and after the event frames to record.

Condition text 1010 allows the user to specify the event condition tested by condition block 370, and used by event analysis step 314 to determine whether an event has occurred. In the illustrative embodiment of FIG. 10, condition text 1010 contains a text string representing a logical expression in a syntax similar to that used by conventional programming languages such as C. The expression combines symbols 500 from FIG. 5, representing elements of active statistics 302, with numeric constants, logical, comparison, and arithmetic operators, and punctuation such as parenthesis, to specify the computation of a true/false value from active statistics 302. Methods for computing a true/false value based on such a text string are well-known in the art.

Figure 15:
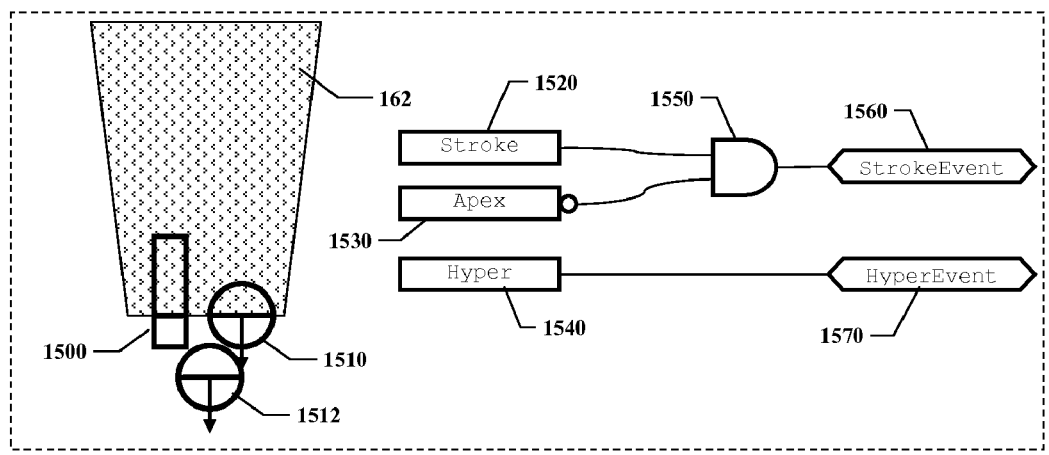
FIG. 15 shows a portion of an exemplary configuration of a vision detector that may be used to detect a label application arm that under- or over-extends during a production cycle.
Figure 16:
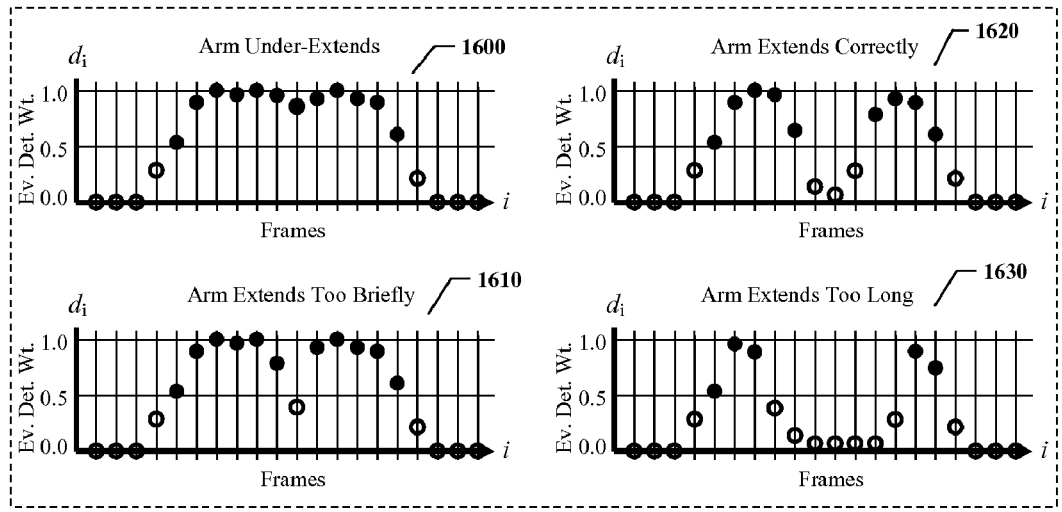
FIG. 16 shows how evidence is weighed to detect under- or over-extension of the arm in the exemplary setup of FIG. 15.

In the illustrative example of FIG. 10, an event has occurred if there are at least two candidate frames and the mean event detection weight is either less than 0.50 or greater than 0.75. An example where such a condition would be useful is shown in FIGS. 15 and 16, described below.

Examples of Use of Illustrative Embodiments

Figure 11:
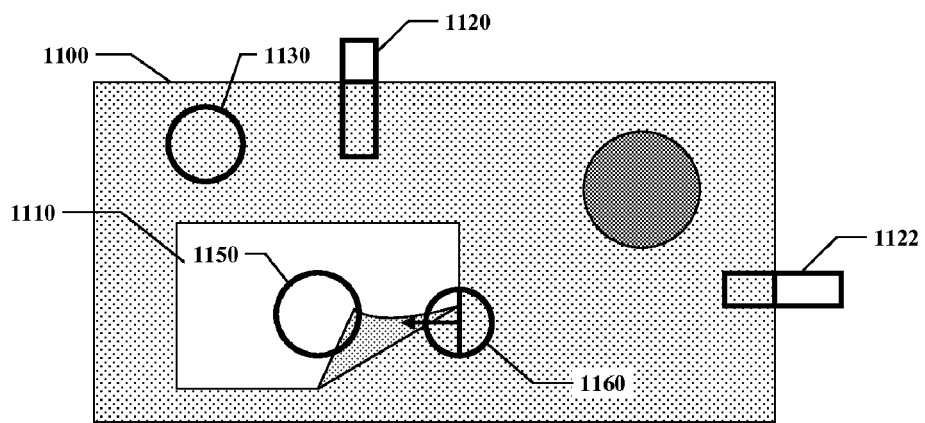
FIG. 11 shows a portion of an exemplary configuration of a vision detector that may be used to detect an improperly applied label on an exemplary object.

FIG. 11 shows an example of how Photos can be used to detect an event corresponding to an object with a misapplied label, such as misapplied label 122 (FIG. 1). FIG. 11 represents an image of an object 1100, which might correspond to object 116 from FIG. 1, containing label 1110, with superimposed graphics representing the Photos, and is displayed on an HMI 630 for a user to view and manipulate. A display of an image and superimposed graphics on an HMI is called an image view.

A Locator 1120 is used to detect and locate the top edge of the object, and another Locator 1122 is used to detect and locate the right edge. A Brightness Detector 1130 is used to help detect the presence of the object. In this example the background is brighter than the object, and the sensitivity threshold is set to distinguish the two brightness levels, with the logic output inverted to detect the darker object and not the brighter background.

Together the Locators 1120 and 1122, and the Brightness Detector 1130, provide the evidence needed to judge that an object is present, as further described below. Clearly, an event corresponding to "object with misapplied label" cannot occur unless an object is present.

An Edge Detector 1160 is used to detect the presence and position of the label 1110. If the label is absent, mis-positioned horizontally, significantly rotated, has a bent corner as shown, or is misapplied in various other ways, the analog output of the Edge Detector would be very low. Of course there are many ways that label 1110 could be misapplied that would not be detected by Edge Detector 1160, and so other Photos might be used as needed to detect failures in any given production situation.

For example, a Brightness Detector 1150 is used to verify that the correct label has been applied. In this example, the correct label is white and incorrect labels are darker colors.

As the object moves from left to right through the field of view of the vision detector, Locator 1122 tracks the right edge of the object and repositions Brightness Detector 1130, Brightness Detector 1150, and Edge Detector 1160 to be at the correct position relative to the object. Locator 1120 corrects for any variation in the vertical position of the object in the field of view, repositioning the detectors based on the location of the top edge of the object. In general Locators can be oriented in any direction.

A user can manipulate Photos in an image view by using well-known HMI techniques. A Photo can be selected by clicking with a mouse, and its ROI can be moved, resized, and rotated by dragging. Additional manipulations for Locators are described in Vision Detector Method and Apparatus.

Figure 12:
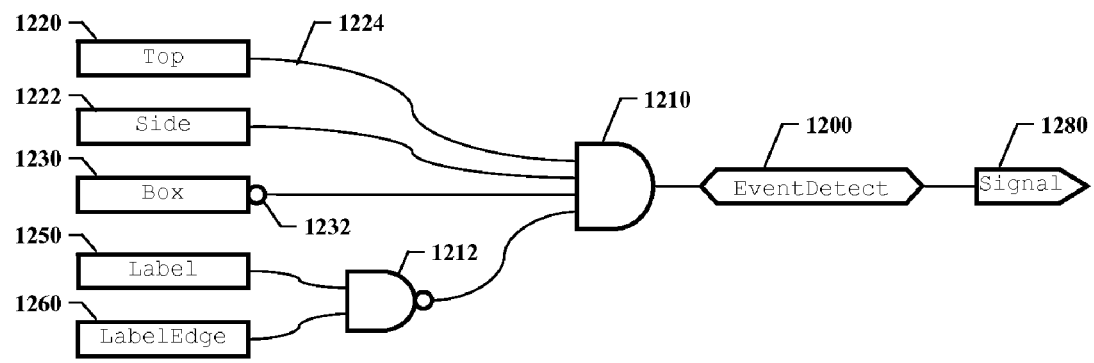
FIG. 12 shows another portion of the configuration corresponding to the exemplary setup of FIG. 11.

FIG. 12 shows a logic view containing a wiring diagram corresponding to the example setup of FIG. 11. A wiring diagram shows all Gadgets being used to detect events and interface to automation equipment, and the connections between logic inputs and outputs of the Gadgets. A wiring diagram is displayed on an HMI 630 for a user to view and manipulate. A display of gadgets and their logic interconnections on an HMI is called a logic view.

Referring still to the wiring diagram of FIG. 12, a Locator 1220 named "Top", corresponding to Locator 1120 in the image view of FIG. 11, is connected to AND Gate 1210 by wire 1224. Similarly, "Side" Locator 1222, corresponding to Locator 1122, and "Box" Detector 1230, corresponding to Brightness Detector 1130, are also wired to AND Gate 1210. The logic output of "Box" detector 1230 is inverted, as shown by the small circle 1232 and as described above to detect the darker object against a lighter background.

In the wiring diagram, Brightness Detector "Label" 1250, corresponding to Brightness Detector 1150, and Edge Detector "LabelEdge" 1260, corresponding to Edge Detector 1160, are wired to AND Gate 1212. The logic output of AND Gate 1212 is inverted to represent the level of confidence that label 1210 is misapplied, and is wired to AND Gate 1210.

The logic output of AND Gate 1210 represents the level of confidence that an object is present and its label has been misapplied, i.e. the level of confidence that an event has occurred. The logic output of AND Gate 1210 is wired to EventDetect Judge 1200 to be used as the event detection weight for each frame. An event condition for EventDetect Judge 1200 suitable for this configuration would be "n>=3 & m>=0.5", although many alternate event conditions would also be suitable depending on the circumstances of the application.

The choice of Gadgets to wire to an EventDetect Judge is made by a user based on knowledge of the application. In the example of FIGS. 11 and 12, a user may have determined that detecting just the top and right edges was not sufficient to insure that an object is present. Note that Locator 1122 might respond to the label's left edge just as strongly as the object's right edge, and perhaps at this point in the production cycle Locator 1120 might occasionally find some other edge in the background. By adding Detector 1130, and requiring all three conditions by means of AND Gate 1210, event detection is made reliable.

When an event is detected, images may be recorded as further described below. Clearly, images corresponding to times prior to the event frames would be most likely to show exactly how the label was misapplied. It is obviously desirable in this case that the vision detector be placed to be able to see the object as close as is practical to the place where the label is applied.

The logic output of EventDetect Judge 1200 is wired to an Output gadget 1280, named "Signal", which controls an output signal from the vision detector than can if desired be connected to automation equipment such as a PLC or actuator. The Output Gadget 1280 is configured by a user as appropriate, as further described in Vision Detector Method and Apparatus. Output Gadget 1280 can produce delayed pulses synchronized to the mark time, as taught in Vision Detector Method and Apparatus, so that the automation equipment can determine when, using time, or where, using encoder count, the event occurred.

A user can manipulate Gadgets in a logic view by using well-known HMI techniques. A Gadget can be selected by clicking with a mouse, its position can be moved by dragging, and wires can be created by a drag-drop operation.

One skilled in the art will recognize that a wide variety of events can be detected by suitable choice, configuration, and wiring of Gadgets. One skilled in the art will also recognize that the Gadget class hierarchy is only one of many software techniques that could be used to practice the invention.

Figure 13:
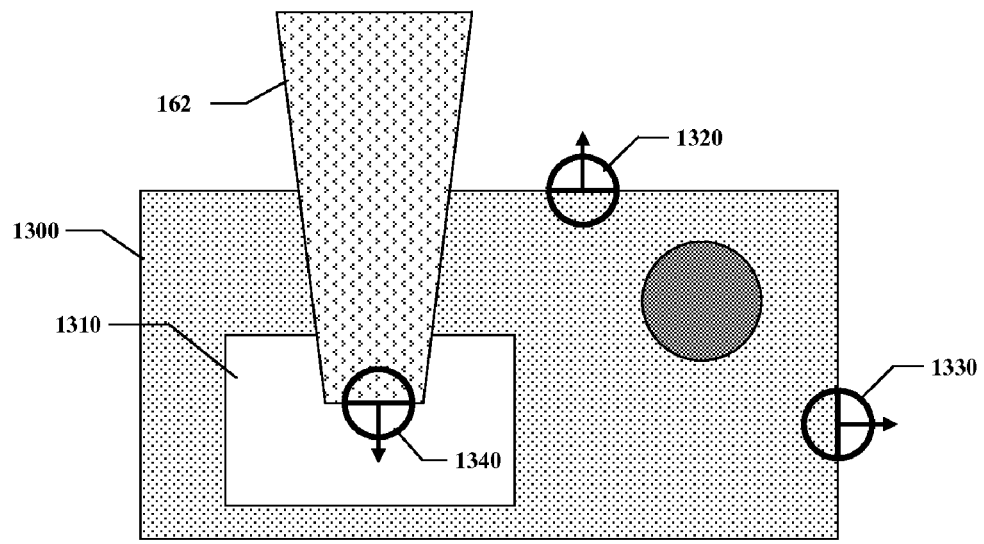
FIG. 13 shows a portion of an exemplary configuration of a vision detector that may be used to detect an exemplary object that is mispositioned relative to a label application arm.

FIG. 13 shows an image view corresponding to another configuration of a vision detector to detect an event that might be useful for the production setup shown in FIG. 1. In this example, the event occurs when labeling arm 162 is fully extended (at the apex of its stroke) but object 1300 is at the wrong position to receive label 1310.

Arm Edge Detector 1340 is placed at a position within the field of view corresponding to the apex of the stroke of labeling arm 162. Note that this position is fixed relative to the field of view—it does not move with the production line, and so there is no need to employ a Locator. Top Edge Detector 1320 and side Edge Detector 1330 are used to verify that object 1300 is in the desired position at the apex of the stroke.

Figure 14:
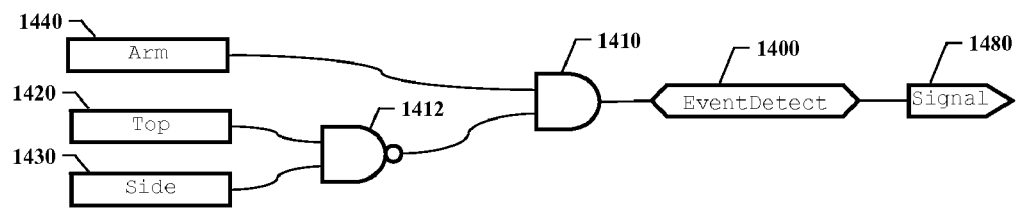
FIG. 14 shows another portion of the configuration corresponding to the exemplary setup of FIG. 13.

FIG. 14 is a logic view showing a configuration of Gadgets corresponding to the image view of FIG. 13, for detecting an event corresponding to an object in the wrong position at the apex of the stroke of the labeling arm 162. "Arm" 1440 corresponds to Arm Edge Detector 1340, "Top" 1420 corresponds to top Edge Detector 1320, and "Side" 1430 corresponds to side Edge Detector 1330.

Using inverted AND Gate 1412 and AND Gate 1410 wired as shown in FIG. 14, EventDetect Judge 1400 receives an event detection weight that represents the level of confidence that object 1300 is not at the position specified by at least one of top Edge Detector 1320 and side Edge Detector 1330 at the time that labeling arm 162 is at the apex of its stroke. An event condition for EventDetect Judge 1400 suitable for this configuration would be "n>=2".

When an event is detected, images may be recorded as further described below. Furthermore, the logic output of EventDetect Judge 1400 is wired to an Output gadget 1480, named "Signal", which controls an output signal from the vision detector than can if desired be connected to automation equipment such as a PLC or actuator. The Output Gadget 1280 is configured by a user as appropriate, as further described in Vision Detector Method and Apparatus.

FIG. 15 shows an image view and a corresponding logic view that together provides yet another configuration of a vision detector to detect an event that might be useful for the production setup shown in FIG. 1. In this example, an event occurs when labeling arm 162 under- or over-extends, meaning that the apex of the stroke is in the wrong place, or when it extends to the correct position but remains there either too briefly or too long for correct label application.

Overextension is easy to detect. An Edge Detector 1512 is placed below the expected apex of the downward stroke of labeling arm 162. Corresponding logic view Edge Detector "Hyper" 1540 is wired to "HyperEvent" EventDetect Judge 1570, which might use the event condition "w>=0.95" to detect an overextended arm. Note that this event condition, using total event detection weight w, would accept a single frame as sufficient evidence if the event detection weight for that frame shows very high confidence, but would require at least two frames if the event detection weights show lower confidence.

For the other conditions, a Locator 1500 is placed to detect that labeling arm 162 is within some range of positions near the apex, and an Edge Detector 1510 is placed to detect that labeling arm 162 is at the apex. Corresponding logic view Locator "Stroke" 1520 and inverted Edge Detector "Apex" 1530 are wired as shown to AND Gate 1550, which is in turn wired to EventDetect Judge "StrokeEvent" 1560. The event detection weight in this configuration represents a level of confidence that labeling arm 162 is near, but not at, the apex of its stroke.

Note that the logic view of FIG. 15 includes the use of two EventDetect Judges. When more than one EventDetect Judge is used, each operates independently so that an event is detected when any of the Judges finds sufficient evidence. Each Judge would perform its own activity analysis step 312 and event analysis step 314, using its own copy of active flag 300, active statistics 302, and inactive statistics 304. Note that the visual analysis steps 310 are performed by other Gadgets, such as Photos and Gates.

FIG. 16 shows how an event condition is formulated for EventDetect Judge "StrokeEvent" 1560 that is suitable for the example configuration of FIG. 15. Shown are four plots of event detection weight $d_i$ versus frame count i, similar to the plot shown in FIG. 4 that was described above.

First plot 1600 shows an arm that has under-extended. The arm moved close to the desired apex for about a dozen frames, but never actually reached the apex. Second plot 1610 shows an arm that has extended to the desired apex, but remained there too briefly, only about one frame, for correct label application. Third plot 1620 shows an arm that extended correctly, reaching the desired apex and remaining there for about three frames. Fourth plot 1630 shows an arm that extended too long, remaining at the desired apex for about seven frames.

The event condition of FIG. 10, "n>=2 & (a<0.50|a>0.75)", is suitable for detecting first plot 1600, second plot 1610, and fourth plot 1630, but not detecting third plot 1620 that corresponds to correct arm extension. The "a<0.50" term detects first plot 1600 and second plot 1610. The "a>0.75" term detects fourth plot 1630. The "n>=2" term insures that a single-frame spurious event is not detected.

Clearly there are many other configurations and event conditions that would also be suitable for detecting mis-extension of a mechanical component such as labeling arm 162, and that will occur to those skilled in the art.

Figure 17:
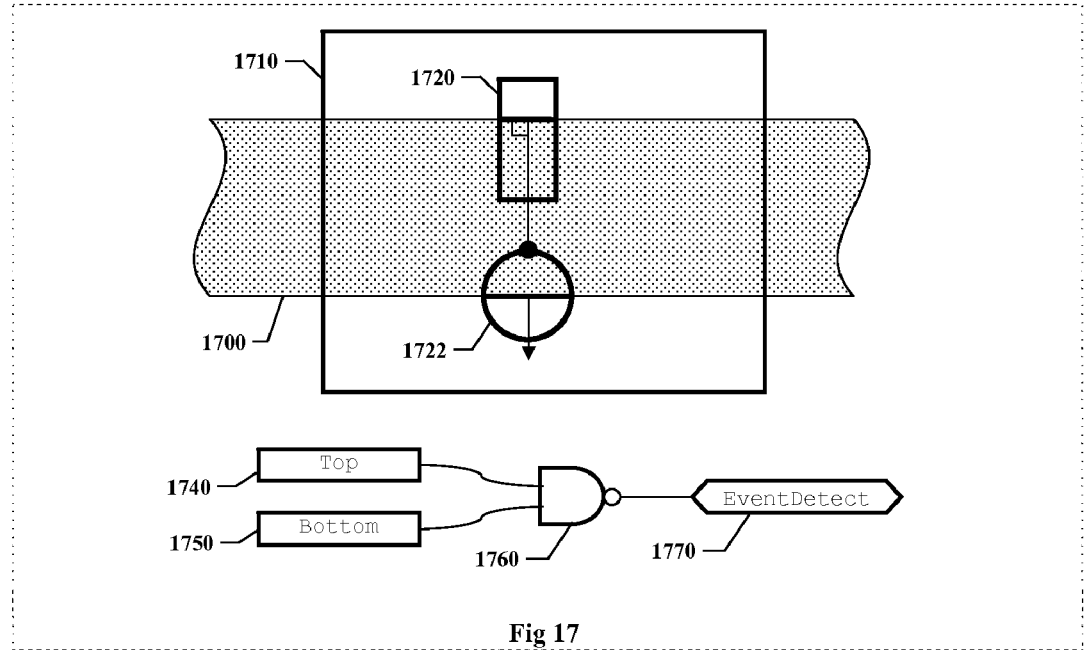
FIG. 17 shows one way to configure the invention to detect events corresponding to flaws on a continuous web.

FIG. 17 illustrates one way to configure the invention to detect and record images of flaws on a continuous web. Image view 1710 shows a portion of continuous web 1700 that is moving past the vision detector.

Locator 1720 and Edge Detector 1722 are configured to inspect the web. If the web breaks, folds over, or becomes substantially frayed at either edge, then Locator 1720 and/or Edge Detector 1722 will produce a false output (logic value<0.5). If the web moves up or down Locator 1720 will track the top edge and keep Edge Detector 1722 in the right relative position to detect the bottom edge. However, if the width of the web changes substantially, Edge Detector 1722 will produce a false output.

In a logic view "Top" Locator 1740 represents Locator 1720, and "Bottom" Detector 1750 represents Edge Detector 1722. These are wired to AND Gate 1760, whose logic output is inverted and wired to EventDetect Judge 1770.

Marking, Stroke Events, and Synchronized Outputs

Figure 18:
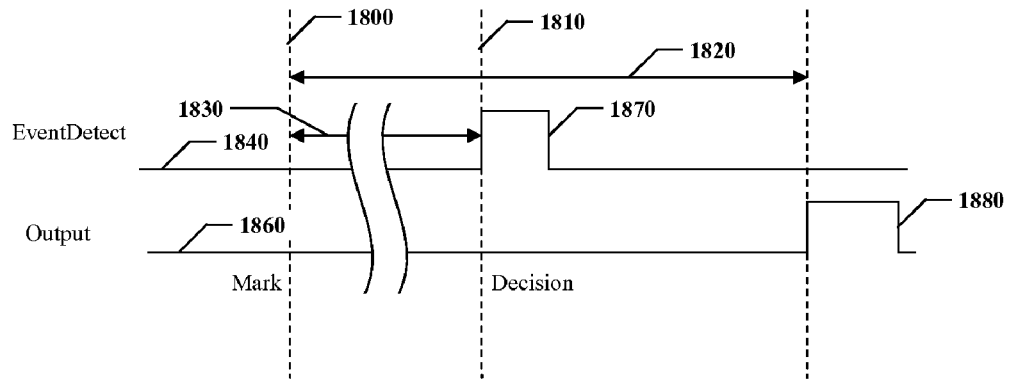
FIG. 18 shows a timing diagram that will be used to explain how output signals are synchronized to the time that an event occurs.

FIG. 18 shows a timing diagram that will be used to explain how vision detector output signals may be synchronized with the mark time. Signal synchronization is desirable for a variety of industrial inspection purposes, such as control of a downstream actuator.

Visual event detection is a novel capability and suggests novel output signal control. It is desirable that a vision detector be able to control some external actuator, either directly or by serving as input to a PLC. This suggests that the timing of output signals be related with reasonable precision to a point in time with some physical meaning, such as when an object passes a particular, fixed point in the production flow (a flow event), or when a mechanical component reaches the apex of a stroke (a stroke event). In the example of FIG. 1 a fixed point could be mark point 150, and in the timeline of FIG. 2 the time is mark times 250 and 252. In the example of FIG. 15, Edge Detector 1510 is positioned at the apex of the stroke of labeling arm 162. In FIG. 18, the time is mark time 1800. Note that an encoder count may be used instead of time.

The present invention can provide outputs synchronized to reasonable precision with the mark time, whether it controls an actuator directly or is used by a PLC or any other external device. One problem, however, is that the present invention detects an event many milliseconds after it occurs, i.e. many milliseconds after the mark time. Furthermore, the delay may be quite variable, depending on how many frames were analyzed and, to a lesser extent, when in the capture/analyze cycle the mark time occurs.

FIG. 18 shows the EventDetect logic output 1840. A detect pulse 1870 appears on EventDetect logic output 1840 when the decision is made at decision point 1810. Decision point 1810 corresponds to the point in time when event block 372 in the flowchart of FIG. 3 is executed. Note that the decision delay 1830 from mark time 1800 to the decision point 1810 will be variable, depending on how many frames were analyzed and, to a lesser extent, when in the capture/analyze cycle the mark time occurs. Therefore the timing of detect pulse 1870 does not convey accurate information about when the event occurred.

The problem of variable decision delay 1830 would apply to any device that attempts to detect events by capturing and analyzing images, and where it is desired to provide a signal indicating when the event occurred to an accuracy that is better than the frame period (inverse of the frame rate). The invention solves the problem by measuring the mark time 1800 and then synchronizing an output pulse 1880 on output signal 1860 to it. The output pulse 1880 occurs at a fixed output delay 1820 from mark time 1800.

The act of measuring the mark time is called marking. The mark time can be determined to an accuracy significantly better than the frame period by linear interpolation, least-squares fit, or other well-known methods, using the known times (or encoder counts) at which the images were captured and the known positions of objects, mechanical components, or anything moving in the field of view, as determined by appropriate Locators. Accuracy will depend on shutter time, overall capture/analysis cycle time, speed of motion, and other factors.

In an illustrative embodiment a user chooses one Locator whose search range is substantially along the direction of motion to be used for marking. For flow events the mark point is arbitrarily chosen to be the center point of the Locator's range—as discussed above, the mark point is an imaginary reference point whose exact position doesn't matter as long as it is fixed. The user can achieve the desired synchronization of output signals by adjusting the delay from this arbitrary time. If an event is detected but the motion does not cross the mark point during the active frames, the mark time can be based on an extrapolation and the accuracy may suffer. For stroke events the mark point is the apex of the stroke, measured as described below. Clearly, other definitions of the mark point can be used to practice the invention.

Note that output signals can only be synchronized to the mark time if output delay 1820 is longer than the longest expected decision delay 1830. Thus any action taken as a result of output pulse 1880, for example operation of an actuator, should be sufficiently downstream of the mark point, which is expected to be the case in almost all applications.

Figure 19:
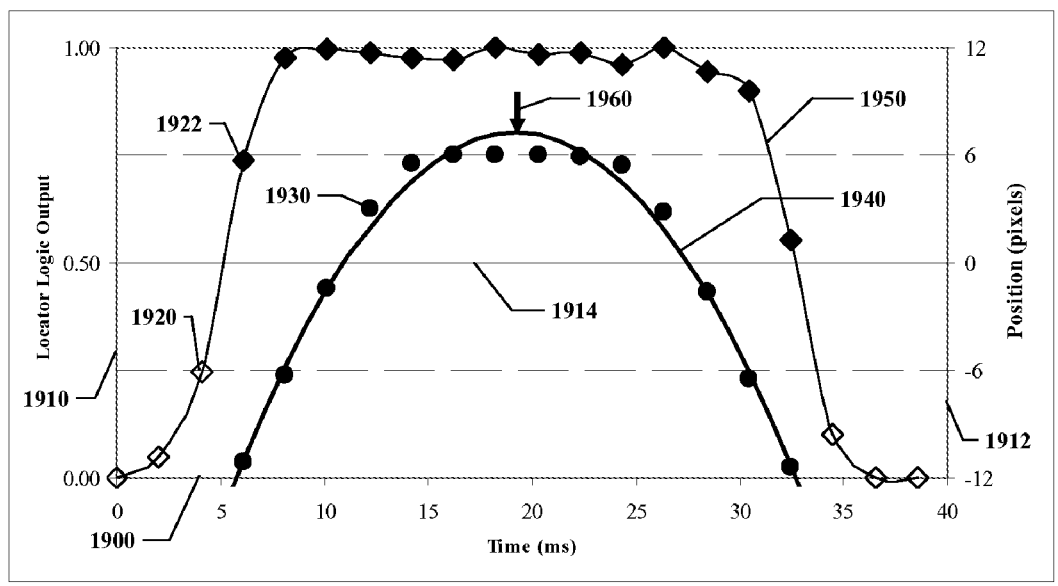
FIG. 19 shows how the mark time is computed for stroke events.

FIG. 19 shows a plot of Locator results as a function of time for a stroke event. The Locator must be configured to search in a direction substantially parallel to the stroke direction, for example Locator 1500 in FIG. 15. Note that a multi-dimensional Locator could also be used, as long as the dimensions searched includes a direction substantially parallel to the stroke direction.

Time, measured from an arbitrary reference point, is plotted on horizontal axis 1900.

The logic output of the Locator is plotted as a sequence of diamond-shaped points, including outline example point 1920 and solid example point 1922, connected by Locator position curve 1950. Note that the Locator measures position only at the discrete times where the diamond-shaped points are plotted, which correspond to frames, and therefore Locator position curve 1950 should be understood to be drawn for the convenience of the reader and does not represent continuous measurements by the Locator. Logic output values, corresponding to the vertical position of the diamond-shaped points, are plotted on first vertical axis 1910. Diamond points drawn in outline, including outline example point 1920, signify low logic output values (below 0.5, corresponding to reference line 1914 in the illustrated embodiment) where there is little confidence that the Locator has found the intended image feature. Diamond points drawn solid, including solid example point 1922, signify high logic output values (at or above 0.5 in the illustrated embodiment) where there is strong confidence that the Locator has found the intended image feature, and therefore that its measured position is valid.

The measured position of the Locator is plotted as a sequence of position points drawn as solid circles, including example position point 1930. Position values, corresponding to the vertical position of the position points, are plotted on second vertical axis 1912 and are measured in pixels from the center of the Locator. Note that position points are only shown for frames where the logic output of the Locator is at or above 0.5, i.e. those frames for which there is strong confidence that the Locator has found the intended image feature.

It can be seen by examining the position points that a mechanical component in the field of view has advanced through the search range of the Locator for about four frames to an apex at around +6 pixels, has held at that apex for around six frames, and then retreated for another four frames before traveling beyond the search range. To compute a specific mark time for this stroke event, the illustrated embodiment uses the position points to compute a best-fit parabola 1940, from which the apex of the parabola 1960 can easily be determined. In the illustrated example, the mark time (apex of the best-fit parabola) occurs at 19.2 milliseconds.

Methods for computing a best-fit parabola from a set of points are well-known in the art. It will be obvious to one skilled in the art that other methods for determining the apex of a stroke event can be used within the scope of the invention. Furthermore, it will be obvious that motions other than the flow and stroke events considered herein can be tracked using methods herein described, and that appropriate curves can be fit, or other techniques used, to determine a mark time for such motions.

FIG. 20 shows a parameter view for user configuration of an Output Gadget, including controls to set output delay 1820 (FIG. 18). Mode control 2000 allows a user to choose how the output signal is controlled. In "straight through" mode, the logic input is passed directly to the output signal without any delay or synchronization. In "delayed" mode, on the rising edge of the logic input an output pulse is scheduled to occur at a time delayed from the most recently measured mark time (or encoder count) by the amount specified by delay controls 2010, and of duration specified by pulse controls 2020. The scheduled pulse may be placed in a FIFO associated with the Output Gadget.

Recording and Retrieval of Images

Figure 21:
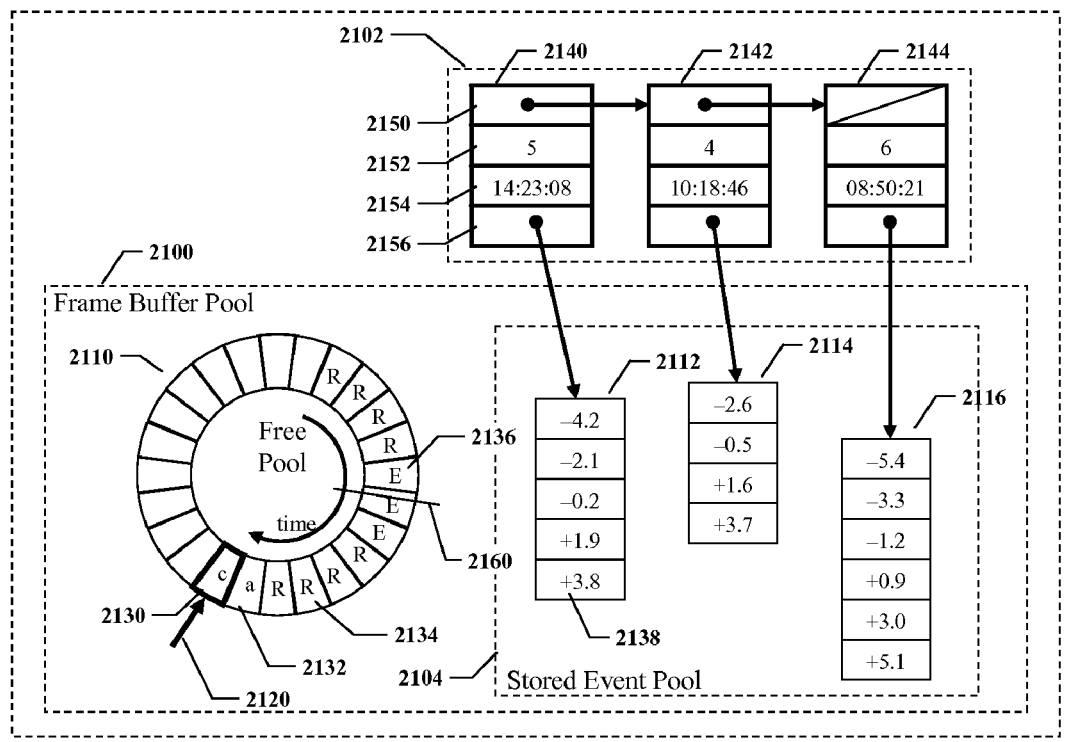
FIG. 21 shows a memory arrangement for recording images of detected events.

FIG. 21 shows details of the organization of a portion of memory 710 (FIG. 7) used in an illustrative embodiment. A frame buffer pool 2100 contains a number of individual frame buffers, such as frame buffers 2130, 2132, 2134, 2136, and 2138, to be used for various purposes. A free pool 2110 is organized as a ring buffer and used to capture and analyze frames for event detection. Write pointer 2120 indicates the next available frame buffer 2130, into which the next frame is captured. Simultaneously with image capture into frame buffer 2130, the previous image in frame buffer 2132 is being analyzed. At some point the ring buffer may become full, at which point the oldest frames will be overwritten.

In an illustrative embodiment where the imager 760 is an LM9630, for example, each frame buffer would contain 128× 100 8-bit pixels. For clarity in the drawing frame buffer pool 2100 is shown to contain only a few dozen elements, but in practice a higher number is desirable. In one embodiment 160 elements are used, which requires just under two megabytes of storage, and which is capable of storing about 0.8 seconds of a production run at 200 frames/second, or about 0.32 seconds at 500 frames/second. Clearly, lower frame rates can be used to increase the amount of time for which images can be stored.

When an event is detected, which may happen many frames after the event occurs, a recent history of captured images will be in free pool 2110. In an illustrative embodiment, free pool 2110 is large enough to hold the event frames and frames prior to and after the event frames in sufficient number for the purposes of the application. At the time an event is detected the recent history may contain none, some, or all of the frames to be recorded, depending on user choices such as recording controls 1050. If the recent history contains all of the frames, they can be recorded immediately as described below. If not, recording happens at a time in the future when all of the frames to be recorded are available.

In the illustrated example, frame buffers marked "R", including example 2134, hold images to be recorded, and "E", including example 2136, hold event frames (also to be recorded). The event occurs at mark time 2160, and is detected during the analysis of the frame in buffer 2134. At the time the event was detected, some but not all of the frames to be recorded are in the recent history. During later analysis of the frame in buffer 2132, it is determined that the recent history now contains all of the frames to be recorded.

To record the frames, the frame buffers are removed from free pool 2110 and added to stored event pool 2104, which includes stored events 2112, 2114, and 2116. If the number of frame buffers in free pool 2110 becomes too small after removing the new stored event, various actions are possible. In one embodiment, event detection ceases until HMI 630 (FIG. 6) uploads the frames in stored event pool 2104 so that the buffers can be returned to free pool 2110. In another embodiment, one or more older stored events may be taken from stored event pool 2104 and placed back in free pool 2104. Those older events will no longer be available for display.

In an illustrative embodiment, frame buffers are never copied. Instead frame buffers are moved between free pool 2110 and stored event pool 2104 by pointer manipulation using techniques well known in the art.

A list of stored events 2102 is maintained, including list elements 2140, 2142, and 2144. List element 2140, for example, contains next element pointer 2150, frame buffer count 2152, result information 2154, and stored event pointer 2156. Result information 2154 may include a timestamp, as illustrated, or other information not shown, such as active statistics 302.

Result information 2154 includes information that applies to the event as a whole. It is further desirable to provide information for each recorded frame, examples of which are shown in the frame buffers of stored event pool 2104. In the illustrated examples, the stored information includes a timestamp that records the capture time of the frame in milliseconds relative to the mark time. Other information (not shown), such as the event detection weight and individual Gadget results, may be recorded as well.

Figure 22:
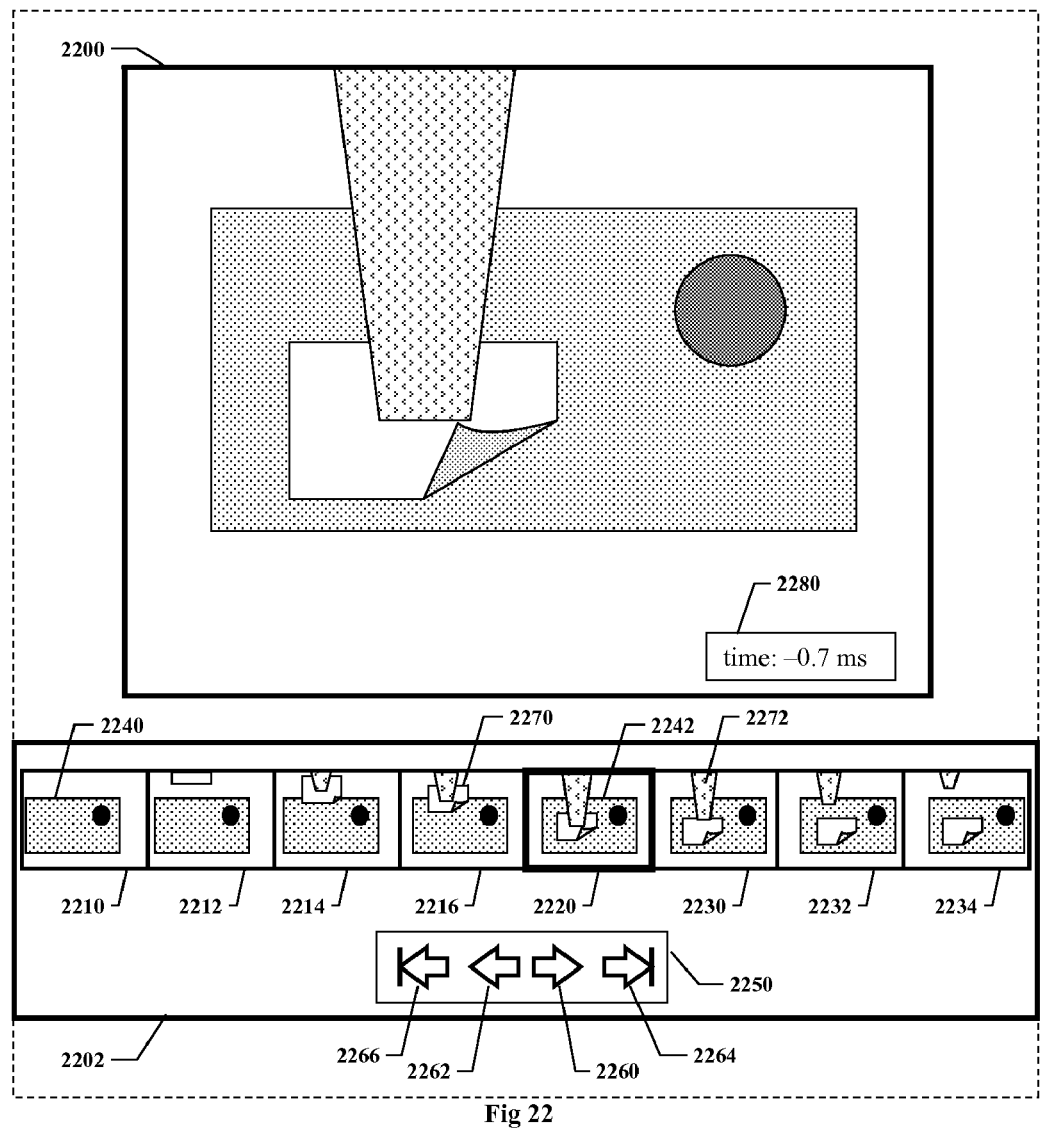
FIG. 22 shows a portion of a graphical user interface containing a filmstrip window and an image view window, and showing images that have been recorded and retrieved corresponding to an event.

Referring back to FIG. 6, the vision detector may be connected to a human-machine interface (HMI) 630, via signals 640, for purposes of configuration. It is also possible for the HMI to be part of the vision detector 600, but this is less preferred because the HMI is generally not needed for event detection, and so one HMI can be shared among many vision detectors. The HMI may run a graphical user interface (GUI) of conventional design, an illustrative portion of which is shown in FIG. 22.

The GUI allows a portion of the recorded images stored in vision detector memory 710 to be displayed for a human user. In the illustrative embodiment of FIG. 22, a filmstrip window 2202 displays up to eight thumbnail images 2210, 2212, 2214, 2216,2220, 2230, 2232, and 2234, each thumbnail image being a low-resolution version of a corresponding recorded image from stored event pool 2104. Generally the thumbnail images correspond to consecutive images of a single event in the record, but other arrangements may be useful, such as skipping some number of images between the corresponding thumbnails.

A set of scrolling controls 2250 is provided in filmstrip window 2202 for advancing the thumbnail images forward or backward within the recorded images of an event, and between events. Next image control 2260 advances forward by one image, and previous image control 2262 advances backward by one image. Next event control 2264 and previous event control 2266 advance the display forward and backward by one event.

Thumbnail 2220 displays a low-resolution image of object 2242, which may correspond for example to object 116 (FIG. 1). Object 2242 also appears in all of the other thumbnails, for example object 2240 in thumbnail 2210, at slightly different viewing perspectives (positions within the field of view) and at different times during the application of label 2270 by arm 2272. By issuing scrolling commands using scrolling controls 2250 the user can advance the recorded images forward or backward to see any desired time interval. Considering the illustrated example images in thumbnails 2212, 2214, and 2216 in particular, in appears that label 2270 may have snagged on the top edge of the object as it was being applied.

In the illustrative embodiment of FIG. 22, the image corresponding to thumbnail 2220, which is shown with a heavy outline and referred to as the selected image, is also displayed at full resolution in image view window 2200. As scrolling commands advance the displayed portion forward and backward, different selected images will move into thumbnail 2220 and be displayed at full resolution in image view window 2200. Other information about the selected image may also be displayed, such as time stamp 2280 that indicates the capture time of the selected image (in milliseconds in this example) relative to the mark time.

The foregoing has been a detailed description of various embodiments of the invention. It is expressly contemplated that a wide range of modifications and additions can be made hereto without departing from the spirit and scope of this invention. For example, the processors and computing devices herein are exemplary and a variety of processors and computers, both standalone and distributed can be employed to perform computations herein. Likewise, the imager and other vision components described herein are exemplary and improved or differing components can be employed within the teachings of this invention. The software elements, GUI designs and layouts, parameter values, and mathematical formulas can all be modified or replaced with equivalents as appropriate for specific applications of the invention. Accordingly, this description is meant to be taken only by way of example, and not to otherwise limit the scope of this invention.

We claim:

1. A method for automatic visual detection of an event, comprising:
    capturing a plurality of frames, each frame in the plurality of frames comprising an image of a two-dimensional field of view in which the event occurs, the event comprising a motion of a predetermined object;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
    selecting a plurality of event frames from the plurality of frames, the plurality of event frames corresponding to a subset of the plurality of event detection weights; and
    determining, responsive to an event analysis of the subset of the plurality of event detection weights, whether the event has occurred.

2. A method for automatic visual detection of an event, comprising:
    capturing a plurality of frames, each frame in the plurality of frames comprising an image of a two-dimensional field of view in which the event occurs;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
    selecting a plurality of event frames from the plurality of frames, the plurality of event frames corresponding to a subset of the plurality of event detection weights;
    determining, responsive to an event analysis of the subset of the plurality of event detection weights, whether the event has occurred; and
    producing a signal that is synchronized with a time at which the event occurs.

3. A method for automatic visual detection of an event, comprising:
    capturing a plurality of frames, each frame in the plurality of frames comprising an image of a two-dimensional field of view in which the event occurs;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
    selecting a plurality of event frames from the plurality of frames, the plurality of event frames corresponding to a subset of the plurality of event detection weights; and
    determining, responsive to an event analysis of the subset of the plurality of event detection weights, whether the event has occurred, the event analysis comprising a text string representing an expression in a syntax substantially similar to the syntax of a conventional programming language.

4. A method for automatic visual detection of an event, comprising:
    capturing a plurality of frames, each frame in the plurality of frames comprising an image of a two-dimensional field of view in which the event occurs, the field of view comprising no more than about 40,000 pixels;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
    selecting a plurality of event frames from the plurality of frames, the plurality of event frames corresponding to a subset of the plurality of event detection weights; and
    determining, responsive to an event analysis of the subset of the plurality of event detection weights, whether the event has occurred.

5. A method for automatic visual detection of an event, comprising:
    capturing a plurality of frames, each frame in the plurality of frames comprising an image of a two-dimensional field of view in which the event occurs;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
    selecting a plurality of event frames from the plurality of frames, the plurality of event frames corresponding to a subset of the plurality of event detection weights;
    determining, responsive to an event analysis of the subset of the plurality of event detection weights, whether the event has occurred; and
    wherein the steps of the method are performed at a rate of not less than two hundred frames per second.

6. A method for automatic visual detection of an event, comprising:
    capturing a plurality of frames, each frame in the plurality of frames comprising an image of a two-dimensional field of view in which the event occurs;
    computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;

selecting, responsive to an activity analysis of the plurality of event detection weights, a plurality of event frames from the plurality of frames, the plurality of event frames corresponding to a subset of the plurality of event detection weights, the activity analysis comprising
entering an active state when the visual analysis computes an event detection weight that indicates sufficient evidence that the event is occurring; and
exiting the active state when the visual analysis computes a plurality of event detection weights that each indicate insufficient evidence that the event is occurring; and
determining, responsive to an event analysis of the subset of the plurality of event detection weights, whether the event has occurred.

7. A method for automatic visual detection of an event, comprising:
using a human-machine interface to specify the event, the human-machine interface comprising a logic view;
capturing a plurality of frames, each frame in the plurality of frames comprising an image of a two-dimensional field of view in which the event occurs;
computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;
selecting a plurality of event frames from the plurality of frames, the plurality of event frames corresponding to a subset of the plurality of event detection weights; and
determining, responsive to an event analysis of the subset of the plurality of event detection weights, whether the event has occurred.

8. A system for automatic visual detection of an event, comprising:
a capture process that captures a plurality of frames, each frame in the plurality of frames comprising an image of a two-dimensional field of view in which the event occurs, the event comprising a motion of a predetermined object;
a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;
a selection process that selects a plurality of event frames from the plurality of frames, the plurality of event frames corresponding to a subset of the plurality of event detection weights; and
an event analysis process that determines, responsive to the subset of the plurality of event detection weights, whether the event has occurred.

9. A system for automatic visual detection of an event, comprising:
a capture process that captures a plurality of frames, each frame in the plurality of frames comprising an image of a two-dimensional field of view in which the event occurs;
a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;
a selection process that selects a plurality of event frames from the plurality of frames, the plurality of event frames corresponding to a subset of the plurality of event detection weights;
an event analysis process that determines, responsive to the subset of the plurality of event detection weights, whether the event has occurred; and
an output process that produces a signal that is synchronized with a time at which the event occurs.

10. A system for automatic visual detection of an event, comprising:
a capture process that captures a plurality of frames, each frame in the plurality of frames comprising an image of a two-dimensional field of view in which the event occurs;
a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;
a selection process that selects a plurality of event frames from the plurality of frames, the plurality of event frames corresponding to a subset of the plurality of event detection weights; and
an event analysis process that determines, responsive to the subset of the plurality of event detection weights, whether the event has occurred, the event analysis process comprising a text string representing an expression in a syntax substantially similar to the syntax of a conventional programming language.

11. A system for automatic visual detection of an event, comprising:
a capture process that captures a plurality of frames, each frame in the plurality of frames comprising an image of a two-dimensional field of view in which the event occurs, the capture process comprising an imager comprising no more than about 40,000 pixels;
a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;
a selection process that selects a plurality of event frames from the plurality of frames, the plurality of event frames corresponding to a subset of the plurality of event detection weights; and
an event analysis process that determines, responsive to the subset of the plurality of event detection weights, whether the event has occurred.

12. A system for automatic visual detection of an event, comprising:

a capture process that captures a plurality of frames, each frame in the plurality of frames comprising an image of a two-dimensional field of view in which the event occurs;

a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;

a selection process that selects a plurality of event frames from the plurality of frames, the plurality of event frames corresponding to a subset of the plurality of event detection weights;

an event analysis process that determines, responsive to the subset of the plurality of event detection weights, whether the event has occurred; and wherein the capture process, the visual analysis process, the selection process, and the event analysis process operate at a rate of not less than two hundred frames per second.

13. A system for automatic visual detection of an event, comprising:

a capture process that captures a plurality of frames, each frame in the plurality of frames comprising an image of a two-dimensional field of view in which the event occurs;

a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;

an activity analysis process that selects, responsive to the plurality of event detection weights, a plurality of event frames from the plurality of frames, the plurality of event frames corresponding to a subset of the plurality of event detection weights, the activity analysis process comprising an active state that is entered when the visual analysis process computes an event detection weight that indicates sufficient evidence that the event is occurring, and that is exited when the visual analysis process computes a plurality of event detection weights that each indicate insufficient evidence that the event is occurring; and an event analysis process that determines, responsive to the subset of the plurality of event detection weights, whether the event has occurred.

14. A system for automatic visual detection of an event, comprising:

a human-machine interface that specifies the event, the human-machine interface comprising a logic view;

a capture process that captures a plurality of frames, each frame in the plurality of frames comprising an image of a two-dimensional field of view in which the event occurs;

a visual analysis process adapted to be carried out by at least one of a collection of digital hardware elements and a collection of computer software instructions residing on a non-transitory computer-readable medium that computes, responsive to the plurality of frames, a plurality of event detection weights, each event detection weight of the plurality of event detection weights corresponding respectively to each frame of the plurality of frames and comprising evidence that the event is occurring in the field of view;

a selection process that selects a plurality of event frames from the plurality of frames, the plurality of event frames corresponding to a subset of the plurality of event detection weights; and an event analysis process that determines, responsive to the subset of the plurality of event detection weights, whether the event has occurred.

15. A method for automatic visual detection of an event, comprising:

capturing a plurality of frames, each frame in the plurality of frames comprising an image of a two-dimensional field of view in which the event occurs, wherein each frame comprises intensity values from a particular integration time;

computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;

selecting a plurality of event frames from the plurality of frames, the plurality of event frames corresponding to a subset of the plurality of event detection weights; and determining, responsive to an event analysis of the subset of the plurality of event detection weights, whether the event has occurred.

16. The method of claim 15 wherein the plurality of frames are captured using an imager with a global shutter.

17. A method for automatic visual detection of an event, comprising:

capturing a plurality of frames, each frame in the plurality of frames comprising an image of a two-dimensional field of view in which the event occurs;

computing, using a processor, responsive to a visual analysis of the plurality of frames, a plurality of event detection weights, each event detection weight of the plurality of event detection weights corresponding respectively to each frame of the plurality of frames and comprising evidence that the event is occurring in the field of view;

selecting, responsive to an activity analysis of the plurality of event detection weights, a plurality of event frames from the plurality of frames, the plurality of event frames corresponding to a subset of the plurality of event detection weights, wherein only those frames in which there is sufficient evidence that the event has occurred are selected as a result of the activity analysis, the activity analysis comprising, entering an active state when the visual analysis computes an event detection weight that indicates sufficient evidence that the event is occurring; and exiting the active state when the visual analysis computes a plurality of event detection weights that each indicate insufficient evidence that the event is occurring; and determining, responsive to an event analysis of the subset of the plurality of event detection weights, whether the event has occurred.

* * * * *